(12) United States Patent
Haddad

(10) Patent No.: US 10,686,772 B2
(45) Date of Patent: *Jun. 16, 2020

(54) ELECTRONIC CREDENTIALS MANAGEMENT

(71) Applicant: Medversant Technologies, LLC, Los Angeles, CA (US)

(72) Inventor: Matthew J. Haddad, Marina del Rey, CA (US)

(*) Notice: Subject to any disclaimer, the term of this patent is extended or adjusted under 35 U.S.C. 154(b) by 444 days.

This patent is subject to a terminal disclaimer.

(21) Appl. No.: 15/483,336

(22) Filed: Apr. 10, 2017

(65) Prior Publication Data

US 2017/0223001 A1    Aug. 3, 2017

Related U.S. Application Data

(63) Continuation of application No. 13/022,604, filed on Feb. 7, 2011, now abandoned.

(60) Provisional application No. 61/302,050, filed on Feb. 5, 2010.

(51) Int. Cl.

| | |
|---|---|
| *H04L 29/06* | (2006.01) |
| *G06F 16/22* | (2019.01) |
| *G06F 16/23* | (2019.01) |
| *G06Q 30/08* | (2012.01) |
| *G06Q 30/00* | (2012.01) |
| *G06Q 10/06* | (2012.01) |
| *G06Q 10/10* | (2012.01) |
| *G06Q 50/22* | (2018.01) |

(52) U.S. Cl.
CPC .............. *H04L 63/08* (2013.01); *G06F 16/22* (2019.01); *G06F 16/2322* (2019.01); *G06Q 10/06* (2013.01); *G06Q 10/10* (2013.01); *G06Q 30/01* (2013.01); *G06Q 30/08* (2013.01); *G06Q 50/22* (2013.01)

(58) Field of Classification Search
CPC ........ G06F 16/22; G06F 21/62; G06F 21/602; G06F 21/6218; G06F 16/951; G06F 21/33; G06F 21/10; G06F 21/64; G06Q 10/06; G06Q 10/10; G06Q 30/01; H04L 63/08; H04L 63/083; H04L 63/0815; H04L 63/102; H04L 63/061; H04L 63/0281; H04L 63/1433
See application file for complete search history.

(56) References Cited

U.S. PATENT DOCUMENTS

2003/0236682 A1* 12/2003 Heyer .................. G06F 19/324
705/2

* cited by examiner

*Primary Examiner* — Maroun P Kanaan
(74) *Attorney, Agent, or Firm* — BakerHostetler

(57) ABSTRACT

A method electronically validates credentials information pertaining to applicants. The method collects credentials information pertaining to applicants in one or more of a plurality of formats and converts the credentials information into a common format of collected credentials information. The converting utilizes a common object model. The method stores the collected credentials information in a database, validates for a plurality of applicants the collected credentials information with external sources through an electronic interface, automatically electronically updates the database with the retrieved data, automatically electronically notifies a user of inconsistencies between obtained third-party credentials data and the collected credentials information pertaining to the applicant, and provides selective electronic access to the third-party credentials data over a communication network to one or more users and to the applicant to which the third-party credentialing data pertains.

36 Claims, 33 Drawing Sheets

Board of Medicine
P.O. Box 30192
Lansing, MI 48909
(517)335-0918
www.michigan.gov/healthlicense

CERTIFICATION OF POSTGRADUATE TRAINING

INSTRUCTIONS TO APPLICANT:

Complete Section I. Type or print your name exactly as it appears on your application. For completion of Section II, send this form to the Director of Medical Education where you completed your postgraduate training. This certification must be submitted directly to the Michigan Board of Medicine by the Director of Medical Education.

SECTION I - APPLICANT INFORMATION

| First Name | Middle Name | Last Name |
|---|---|---|
| First Name | Middle Name | Last Name |
| Social Security Number | Date of Birth | |
| Social Security Number | Date of Birth | |
| Street Address | | |
| Street Address | | |
| City | State | Zip Code |
| City | State | ZIP Code |
| Daytime Telephone Number | All Previous Names and/or Birth Name Used if applicable | |
| Daytime Telephone Number | All Previous Names and/or Birth Name Used if applicable | |

Peer Reference Form

Overview
Profile
Peers
Affiliations
Calendar
Documents

Name : Dr. Mark Geller      View Reference History

As part of credentialing process, we would appreciate information requested below. ProviderSource will hold the information in confidence, and we would appreciate your complete candor in responding to this inquiry. Thank you for your prompt attention to this request. ──── 2300

1. How long have you known the applicant

2. Your knowledge of the applicant's competence is based on: ──── 2302

☐ Personal Observation    ☐ Program Director    ☐ Colleague

☐ Other _____

3. Please describe your knowledge of the candidate's professional competence:
   (1. Excellent 2. Good 3. Fair 4. Poor 5. No Knowledge)

|  | 1 | 2 | 3 | 4 | 5 |
|---|---|---|---|---|---|
| Basic Clinical Knowledge | ○ | ○ | ○ | ○ | ○ |
| Professional Judgement | ○ | ○ | ○ | ○ | ○ |
| Competence/Skills | ○ | ○ | ○ | ○ | ○ |
| Sense of Responsibility | ○ | ○ | ○ | ○ | ○ |
| Patient Management | ○ | ○ | ○ | ○ | ○ |
| Provider/Patient Relationship | ○ | ○ | ○ | ○ | ○ |
| Cooperativeness/Ability to Work with Others | ○ | ○ | ○ | ○ | ○ |

⎬ 2304

4. Comments: _____

ELECTRONIC CREDENTIALS MANAGEMENT

CROSS-REFERENCE TO RELATED APPLICATIONS

This U.S. non-provisional patent application claims priority under 35 U.S.C. § 120 as a continuation of U.S. patent application Ser. No. 13/022,604, entitled "System and Method for Peer Referencing in an Online Computer System," filed Feb. 7, 2011, which claims priority under 35 U.S.C. § 119 to U.S. Provisional Patent Appl. No. 61/302,050, entitled "Electronic Credentials Management System with Visual Object Mapping Tool and Peer Network Portal," filed Feb. 5, 2010. The entire disclosures of U.S. patent application Ser. No. 13/022,604 and U.S. Provisional Patent Appl. No. 61/302,050 are incorporated herein by reference.

This application is also related to (1) U.S. Pat. No. 8,850,304, entitled "System and Method for Visually Mapping and Automatically Completing Electronic Forms," which issued on Sep. 30, 2014 from patent application Ser. No. 13/022,550, filed on Feb. 7, 2011, and also claiming priority to U.S. Provisional Patent Appl. No. 61/302,050; and (2) U.S. Pat. No. 7,529,682, entitled "Electronic Credentials Verification and Management System," which issued on May 5, 2009 from patent application Ser. No. 13/022,550, filed on Dec. 11, 2002. U.S. patent application Ser. No. 13/022,604 incorporated by reference U.S. patent application Ser. No. 13/022,550 and U.S. Pat. No. 7,529,682, the disclosures of both of which are also incorporated by reference in this application.

TECHNICAL FIELD

In one respect, this disclosure generally relates to electronic management systems, and more particularly, to a system for storing, continually verifying and retrieving credentials records in a global network environment. In another respect, this disclosure generally relates to systems and methods for managing and completing electronic forms, and more particularly, to a system and method for mapping healthcare administrative forms to a common object model for automating the completion of such forms. In yet another respect, this disclosure generally relates to an online computer system that allows healthcare providers to connect via an online portal, and more particularly, to a peer network portal that allows healthcare providers to generate a network of peers for facilitating the obtaining of peer references.

BACKGROUND

Credentials Verification and Management

Professionals are frequently required to be licensed and to undergo rigorous screening before practicing their profession. For example, healthcare practitioners, such as physicians, are typically required by federal, state and regulatory agencies to have a thorough background check when initially applying to hospitals, health maintenance organizations, independent physician associations and other like healthcare entities. In addition, once approved by an entity, the practitioner's background must be re-checked at periodic intervals through the course of his tenure with the healthcare entity. However, practitioner background checks create large volumes of data that must be stored, validated, analyzed and updated on a continuous basis. Such data includes at a minimum, education, training, licensure and license sanctions, work experience, malpractice insurance coverage, malpractice history and peer references.

It may be possible for professional organizations to use electronic data processing systems to automate the creation, use and maintenance of credentials in a manner that is similar to systems currently employed for the storing and management of other occupational data. However, these electronic data processing systems often do not handle data in the wide variety of data formats that may typically be used for credentials verification by healthcare entities. The wide variety of data formats for the collection of credentials information often hinders electronic processing and maintenance of practitioner files. Moreover, many professional practitioners have traditionally used paper-based forms to document their credentials information.

In addition, under current practices there may be significant duplication of credentials information. For example, within healthcare systems similar credentials information may exist in remote practitioner files located at clinics, hospitals, laboratories and physicians' offices. However, due to inefficiencies with current methods of data collection and verification, including the inability of current electronic systems to allow for the sharing of a central record of practitioner data, it is common for practitioner files at one entity to have credentials information that differs from the same practitioner files at another entity within the same system. Such differences may include missing data as well as differing experience, performance and license sanctions histories.

Further, credentials information in the practitioner files is generally not available for review by the practitioners themselves to confirm or dispute the information. Moreover, relationships among specific credentials information documented in a practitioner file such as adverse actions, gaps in work history and misstatements on the credentials application may not be apparent unless manually pulled together as a whole.

In addition, in the current environment, specific credentials information is difficult to access when needed for analysis due to its paper-based nature. Moreover, in current systems the use of a practitioner's file by one entity can preclude its simultaneous use by another entity. Under these circumstances, entities have difficulty ascertaining the fitness of their practitioners to provide services for their customers.

Data Mapping

There is a general need for mapping healthcare data, especially healthcare provider information, such as demographics, license, education, and billing information, to enable the populating of administrative forms. Healthcare providers (also referred to as doctors or practitioners) are often required to fill out hundreds of various forms that are exchanged with other providers and healthcare entities to maintain their practice as well to maintain insurance and hospital affiliations. For example, a specialist applying for credentialing may need to complete a form for one healthcare entity that contains the same core information he or she just filled in a different form used to apply for enrollment and contracting for another healthcare entity.

One common method of auto-completing or pre-populating forms is one-to-one mapping of database fields to form fields, via manual coding. Such mapping generally requires re-mapping, at a programming level, of each relationship as new forms are added to the system. As the result, the process may take weeks to map one form and does not provide reasonable scalability to deal with the vast amount different forms in the healthcare industry.

Another method for pre-populating forms includes extracting data from a database into a separate flat file. An offline form mapping tool is then utilized to map form fields with flat file data fields to eventually populate the form with extracted data. This process is also cumbersome and time consuming due to lack of automation and reusability.

Accordingly, there is a need for a system and method for automating the mapping and completion of different forms that is more efficient and more scalable than existing methodologies.

Peer Referencing

One problem in the current healthcare industry is the ability of a provider to readily find other providers who are qualified to provide peer references. When a healthcare organization appoints an individual to the medical staff or grants initial clinical privileges, the common regulation from the Joint Commission requires that all information about the applicant be available and verified before any action can be taken. Among others, peer references are part of the more critical information to be requested and verified.

Healthcare peer referencing differs from typical reference checking in other industries. Peer references are reviewed according to very rigorous standards, and thus, not all providers are qualified to provide references. For example, the joint commission generally requires hospitals to follow these standards for acceptable peer references: an applicant's peers need to provide specific information on medical responsibilities, character, training, competence, and health status as they affect performance. The scope of peer references varies depending on the type of provider and level of clinical privileges to be granted. Many organizations provide the peer with a privileging list that is used to grant an applicant's privileges. Peers are asked to comment on the applicant's ability to perform the tasks listed on the privileging list. One of the goals of this strict process is to keep the reference less subjective and biased.

A peer is typically defined as someone from the same discipline with essentially equal qualifications. In order to be able to provide a reference, the peer must generally be familiar with the individual's actual performance in that discipline. For instance, in an allied health provider credentialing process, a nurse practitioner, physician assistant, psychologist, or social worker ideally should have another individual from the same discipline to be the peer, and the organization should attempt to obtain such references. This could be someone within the same organization or someone from outside the organization.

In situations where there is no nurse practitioner, physician's assistant, psychologist, or social worker who can provide a peer reference, it is generally acceptable for a physician or D.O. with essentially equal qualifications, who is familiar with the allied health practitioner's performance, to provide the reference. For example, an internist could provide a reference for a physician assistant; an anesthesiologist could provide a reference for a nurse anesthetist; a psychiatrist could provide a reference for a psychologist; and a psychologist with similar responsibilities could provide a reference for a social worker.

Due to these complicated rules and criteria, as well as the current state of manual process for contacting and collecting peer references, many organizations are spending vast amount of time and resources to meet regulatory standards before clinical privileges can be granted.

In recent years, Internet, email and electronic messaging technologies have been widely adopted to transmit information among users. Social networking sites like LinkedIn and Facebook have connected hundreds of millions people to share common interests and activities. However, nothing has been done to address specific nature and needs of peer referencing in the provider credentialing field. Thus, there is a need for an electronic system that receives an maintains information about peer providers so that those providers can be readily identified based on qualifying criteria, and so that communication with the qualifying peer providers can be easily facilitated. There is also a need for a qualifying peer provider to efficiently provide a peer reference upon request.

SUMMARY

Credentials Verification and Management

In one aspect of the present invention a method for electronically verifying information includes requesting credentials information from applicants in a plurality of formats, collecting received credentials information from the applicants in a common format through an interface to a global network, storing collected credentials information in a dynamic database and verifying collected credentials information with external sources through an electronic interface.

Data Mapping

According to one embodiment, the present invention is directed to a computer apparatus and a method for mapping fields of an electronic form to a common object model. The computer apparatus includes a data storage device, a display device displaying a mapping area, a processor, and a memory that is operably coupled to the processor and that stores program instructions therein. The processor is operable to execute the program instructions. The program instructions include displaying on the display device a plurality of objects of the common object model, and displaying on the display device a plurality of fields of the electronic form. The program instructions further include receiving user selection of one or more of the displayed objects of the common object model, and displaying the selected one or more objects in the mapping area. User selection of one of the displayed fields of the electronic form is also received, and the selected field is displayed in the mapping area. The program instructions further include identifying a type of association between the one or more objects in the mapping area, and the field in the mapping area. The program instructions then generate a mapping entry in a map file of the data storage device, mapping the one or more objects in the mapping area, to the field in the mapping area. The mapping entry includes the identified type of association. The map file is then configured to be retrieved for automatically populating the plurality of fields of the electronic form with data stored for the objects mapped to the plurality of fields.

According to one embodiment of the invention, the user selection of the one or more of the displayed objects includes dragging and dropping the selected one or more of the objects to the mapping area. Similarly, the user selection of one of the displayed fields includes dragging and dropping the displayed field to the mapping area.

According to one embodiment of the invention, the displaying the plurality of objects includes displaying identifiers for the objects in a list format.

According to one embodiment of the invention, the identifying the type of association includes displaying a list of associations, and receiving a user selection of one of the associations from the list.

According to one embodiment of the invention, the type of association indicates a direct mapping between a single object in the mapping area, and the field in the mapping area.

According to one embodiment of the invention, the type of association indicates mapping a plurality of the objects in the mapping area, to the field in the mapping area.

According to one embodiment of the invention, the type of association identifies an aggregation rule for aggregating data stored for the plurality of objects in the mapping area, when populating the field on the form mapped to the plurality of objects.

According to one embodiment of the invention, the type of association identifies a conversion rule for converting an aspect of data stored for the one or more objects in the mapping area, when populating the field on the form mapped to the one or more objects. The converting may be converting a format of the data.

According to another embodiment, the present invention is also directed to a computer apparatus and method for automatically populating an electronic form. The computer apparatus includes a data storage device storing a plurality of forms and a map file for each of a plurality of forms. Each of the forms includes one or more fields. The computer apparatus also includes a display device, a processor, and a memory operably coupled to the processor. The memory stores program instructions for being executed by the processor. The program instructions include populating a common object model based on the received data, receiving user selection of a form in the data storage device to be populated, and retrieving a map file for the selected form from the data storage device. The map file maps each of the one or more fields of the form to one or more objects of the common object model, and further indicates a type of association for each mapping. The program instructions also include retrieving data stored for the one or more objects of the common object model mapped to the one or more fields of the form, and processing the retrieved data based on the type of association indicated for the retrieved data in the retrieved map file. The program instructions then automatically populate the one or more fields of the form based on the processed data. The populated fields are then displayed on the display device.

According to one embodiment of the invention, the program instructions further include displaying a universal form corresponding to the common object model, and prompting the user to enter information requested on the universal form.

According to one embodiment of the invention, the automatically populating the one or more fields based on the processed data is without manual input of the data by the user into the one or more fields of the form.

These and other features, aspects and advantages of the present invention will be more fully understood when considered with respect to the following detailed description, appended claims, and accompanying drawings. Of course, the actual scope of the invention is defined by the appended claims.

According to one embodiment, the present invention is directed to a computer apparatus and a method for generating a network of peers for obtaining peer references. The computer apparatus includes a data storage device, a processor, and a memory that is operably coupled to the processor and that stores program instructions therein. The processor is operable to execute the program instructions. The program instructions include receiving profile information for a particular healthcare provider, storing the profile information in the data storage device, and automatically identifying one or more other healthcare providers who are qualified to provide a peer referral for the particular healthcare provider. The automatically identifying of the other healthcare providers includes automatically comparing the profile information of the particular healthcare provider with profile information of other healthcare providers in the data storage device for determining whether one or more qualification criteria have been satisfied. The program instructions further entail including the identified healthcare providers in a peer network for the particular healthcare provider for transmitting a request for peer referral to one or more of the identified healthcare providers.

According to one embodiment of the invention, the program instructions further include transmitting an invitation to the identified healthcare providers to join the peer network for the particular healthcare provider.

According to one embodiment of the invention, the request for peer referral includes a link to a peer referral input form.

According to one embodiment of the invention, the program instructions further include receiving peer referral information entered in the peer referral input form; and storing the peer referral information in the data storage device. Fields of the peer referral input form may be mapped to objects of a common object model. In that case, the program instructions for storing the peer referral information includes program instructions for populating the objects of the common object model with the peer referral information.

According to one embodiment of the invention, the program instructions further include identifying a peer referral form; and automatically populating fields of the peer referral form based on the peer referral information stored in the common object model.

According to one embodiment of the invention, the program instructions further include maintaining a list of the identified healthcare providers; and updating the list in response to a monitored event.

According to one embodiment of the invention, the monitored event is change of profile information of the particular healthcare provider or the other healthcare providers.

These and other features, aspects and advantages of the present invention will be more fully understood when considered with respect to the following detailed description, appended claims, and accompanying drawings. Of course, the actual scope of the invention is defined by the appended claims.

BRIEF DESCRIPTION OF THE DRAWINGS

The present invention will become better understood with regard to the following description, appended claims, and accompanying drawings, in which:

FIG. 19 is a screen shot of an exemplary screen displaying a form that has been selected for mapping, according to one embodiment of the invention;

FIG. 20 is a screen shot of an exemplary screen with a list of conversion options in a conversion drop down list, according to one embodiment of the invention;

FIG. 21 is a screen shot of an exemplary screen with a list of aggregation options in an aggregation drop down list, according to one embodiment of the invention;

FIG. 22 is a screen shot of an exemplary mapping table of a map file according to one embodiment of the invention; and FIG. 23 is a screen shot of the form depicted in FIG. 19, with exemplary data filled in according to the mapping schema in the mapping table of FIG. 22, according to one embodiment of the invention.

FIG. 27 is an exemplary screen shot of a screen listing peers that are available for inviting into a user's peer network according to one embodiment of the invention.

FIG. 28 is an exemplary screen shot of an invitation message for inviting peers to join a user's network according to one embodiment of the invention.

FIG. 32 is an exemplary screen shot of a screen displaying a universal peer reference form according to one embodiment of the invention.

DETAILED DESCRIPTION

Credentials Verification and Management

An exemplary embodiment of a web based credentials acquisition, storage, verification and audit system (WebCVO) automates and simplifies existing methods of credentials information collection, verification, audit, maintenance and retrieval. In contrast to other systems, the described exemplary embodiment creates and maintains all credentials information electronically and thus can eliminate or supplement the creation and maintenance of physical data records. An exemplary WebCVO may further provide an intuitive, easy-to-use, web-based interface that allows users to capture and analyze credentials information quickly and efficiently. In accordance with an exemplary embodiment, credentials information may be entered into the electronic credentials system from paper-based forms or may be imported from electronic storage devices (diskette, CD-ROM, tape or the like). Alternatively, credentials information may also be scanned in through the use of a teleform or directly entered by a practitioner into the WebCVO system.

In addition, the described exemplary WebCVO system may include the capability to manage and report on a wide variety of credentials information formats, including credentials information from external sources, such as licensing organizations and governmental databases. In accordance with an exemplary embodiment, the WebCVO system may continuously access external sources to validate current credentials information. The WebCVO system may then alert the practitioner and all entities to which that practitioner is assigned of any information not validated by an external source and to information reported by the source but not recorded in the practitioner's credentials record.

The described exemplary WebCVO system may also prompt practitioners to renew credentials information prior to the expiration of that information. In addition, an exemplary WebCVO system can also incorporate a practitioner's legacy data, such as quality information, into the practitioner record as well as legacy data from mainframe computers.

Figure 1:
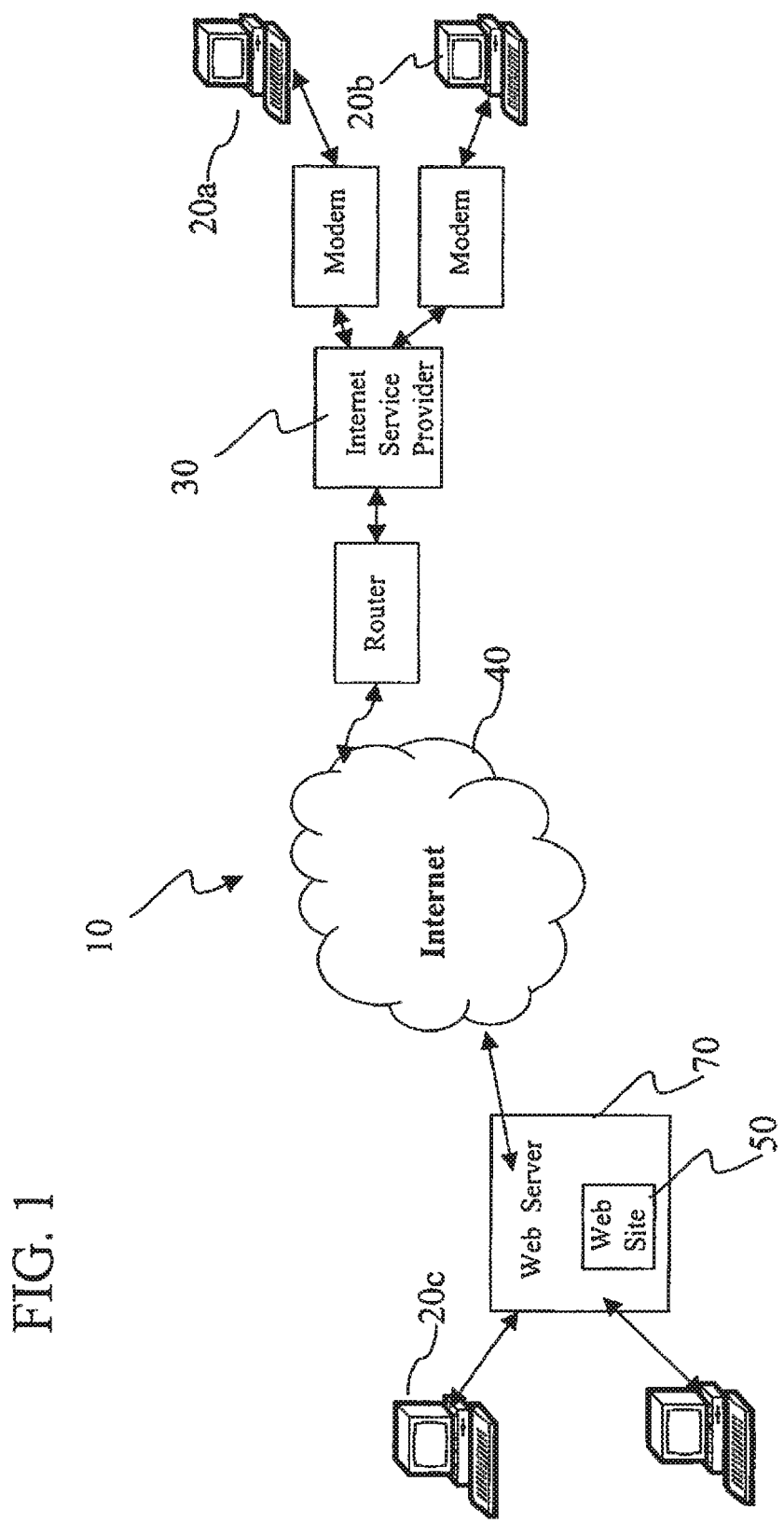
FIG. 1 is a simplified block diagram of an electronic credentials verification system in accordance with an exemplary embodiment of the present invention.

FIG. 1 illustrates an exemplary electronic credentials system 10. The described exemplary electronic credentials system 10 includes multiple remote devices 20a and 20b coupled to one or more web servers 30 through a remote communication network 40. The communication network may refer to a network or combination of networks spanning any geographical area, such as a local area network, wide area network, regional network, national network, and/or global network. The Internet is an example of a current global computer network. In addition, the communication network may be a hardwire network, wireless network, or a combination of hardwire and wireless networks.

Hardwire networks may include, for example, fiber optic lines, cable lines, ISDN lines, copper lines, etc. Wireless networks may include, for example, cellular systems, personal communications service (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

The remote devices 20a-20b may be general purpose computing devices that allow users to remotely communicate with the web server over the communication network 40. The computing devices may be any processor controlled device that permits access to the communication network, including terminal devices, such as personal computers, workstations, servers, clients, mini-computers, main-frame computers, laptop computers, a network of individual computers, mobile computers, palm-top computers, hand-held computers, set top boxes for a television, other types of web enabled televisions, interactive kiosks, personal digital assistants, interactive or web enabled wireless communications devices, mobile web browsers, or a combination thereof.

The computers may comprise one or more input devices such as a keyboard, mouse, touch pad, joystick, pen input pad, and the like. The computers may also possess an output device, such as a visual display and an audio output. One or more of these computing devices may form a computing environment.

An exemplary web server 70 preferably hosts a website 50 comprising one or more interrelated web page files and other files and programs. The files and programs may be accessed via a communications network 40 such as the Internet, by sending for example, a hypertext transfer protocol (HTTP) request specifying a uniform resource locator (URL) that identifies the location of one of said web page files, wherein the files and programs are owned, managed or authorized by a single entity. Such files and programs can include, for example, hypertext markup language (HTML) files, common gateway interface (CGI) files, and Java applications.

In an exemplary embodiment, the web page files preferably include a home page file that corresponds to a home page of the website. The home page can serve as a gateway or access point to the remaining files and programs contained within the website. In one embodiment, all of the files and programs may be located under, and accessible within, the same network domain as the home page file. Alternatively, the files and programs can be located and accessible through several different network domains.

The described exemplary website may use encryption technology such as for example secure socket layer (SSL) encryption and digital certificates to maintain the integrity and confidentiality of electronic transmissions to and from the Web server 70. In the described exemplary embodiment message data is encrypted using a randomly generated key that is further encrypted using the recipient's public key. This is referred to as the "digital envelope" of the message which is sent to the recipient with the encrypted message. The recipient decrypts the digital envelope using a private key and then uses the symmetric key to unlock the original message.

Figure 2:
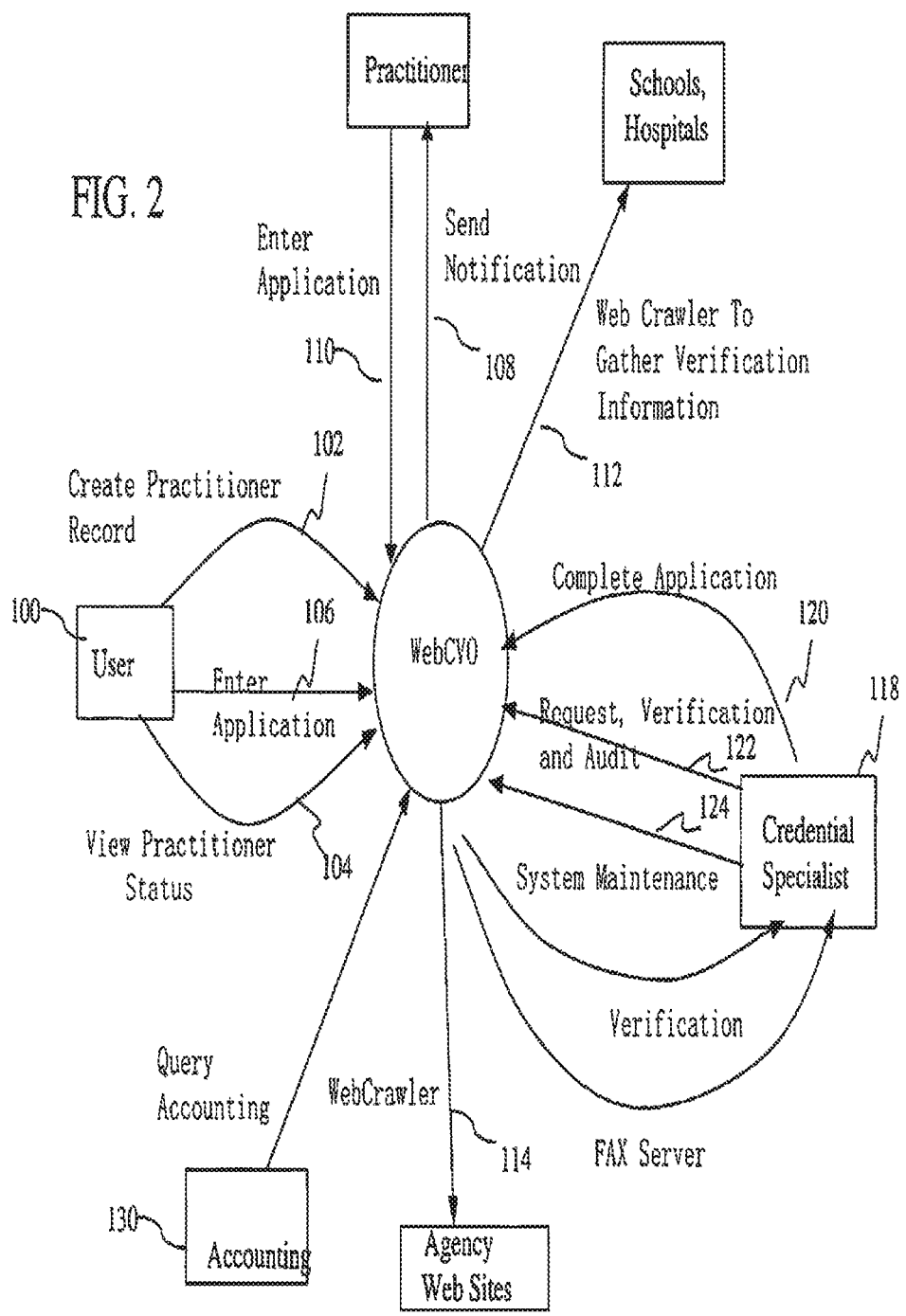
FIG. 2 is a graphical illustration of the relationship of the applicant, client, electronic verification sources and non-electronic verification sources in accordance with an exemplary embodiment of the present invention.

FIG. 2 graphically illustrates the relationship of the practitioner, client, electronic verification sources and non-electronic verification sources within an exemplary electronic credentials system. The described exemplary electronic credentials system gives users considerable freedom to manage, maintain and utilize the functionality of the system. For example, users 100 can create new practitioner accounts 102 including a credentials application which a practitioner may then complete. In an exemplary embodiment, the system may automatically send a notification 108 to the practitioner preferably instructing the practitioner to log on to the system and input his credentials information 110.

An exemplary system may send the notification by any of a number of conventional means, such as by email, fax, letter or a combination thereof. In one embodiment an exemplary system may assign a contact method based upon the practitioner's preference for receiving credentials information requests. Further, an exemplary system may automatically send an email to practitioners which includes instructions on how to access the credentials system electronically (e.g. online) as well as requests for the updating or clarifying of credentials information. An exemplary system may compare existing data to newly entered data and archive existing data to a history table.

In one embodiment, the electronic credentials system p may automatically forward a fax with instructions for online access or instructions for receiving a blank credentials application via Internet download, fax or mail to a practitioner. The described exemplary electronic credentials system may also automatically fax or print for mailing complete credentials packages, including instructions and application materials. The described exemplary system may also automatically contact practitioners opting to complete a paper application via fax or letter generation for the completion, update and clarification of their credentials.

In one embodiment a user may also view the status of an existing practitioners 104 credential application or re-verification, plan committee and continuing education meetings and create customized pages for their own use 106. In addition, the described exemplary system may identify verification requirements for a particular practitioner including the parameters for handling adverse information. The described exemplary system may then automatically contact various entities such as, for example, schools, hospitals, or peers to request verification information 112, via for example, a web crawler, link, or other conventional method of querying a database.

For example, in an online verification system an encrypted request for verification may be included as parameters on an HTTPS query string to verification sites. In one embodiment the request may further include payment of a verification fee. The described exemplary system may also auto-generate email, fax or letter requests to non-electronic verification sources including payment of verification fees.

An exemplary system may send requests for verification information by fax, letter or email (if choose by phone, an exemplary system may schedule phone calls for WebCVO credentials specialists). An exemplary system may also automatically check the websites of all government agencies (for example, via a web crawler, link or other conventional method of querying a database), or other regulatory bodies for information related to the practitioner's credentials 114. In addition, an exemplary system may make follow-up requests for verification information according to a pre-set schedule.

The described exemplary system may compare the verification information received from external sources to the credentials information submitted by the applicant. An exemplary system may then auto-update the database with matched information or manually update the database through the use of electronic work prompts or ticklers.

For example, in an exemplary embodiment, a credentials specialist 118 may compile the responses to the requests for verification information and perform various other tasks to complete the application process 120. A credentials specialist may then utilize a fax server or other similar means to verify and audit the practitioner information 122.

In an exemplary embodiment, the received verification information may be archived in an online data repository, allowing web access and tracking. For example, in the described exemplary embodiment, electronic information received from verification sites may be stored as digital images in an applicants database. Similarly, verification information received from non-electronic sources may be scanned and stored as scanned images. The described exemplary system may further comprise an accounting component that tracks all individual itemized charges in accordance with particular contract requirements 130.

An exemplary embodiment of the present invention may also provide instant access to a practitioner's electronic credentials record by authorized entities from any geographic location. For example, the described exemplary system may provide authorized entities to access and update practitioner files using, for example, the Internet. To enable complete replacement of physical records, the present invention permits practitioners to electronically annotate practitioner data. Thus, a practitioner can enter and update credentials information, acknowledge that he or she has reviewed posted credentials information. A practitioner may also provide explanations for any information not validated by an external source or for information reported by a source, not currently posted to the practitioner's record, all by electronically annotating a practitioner's record.

Figure 3:
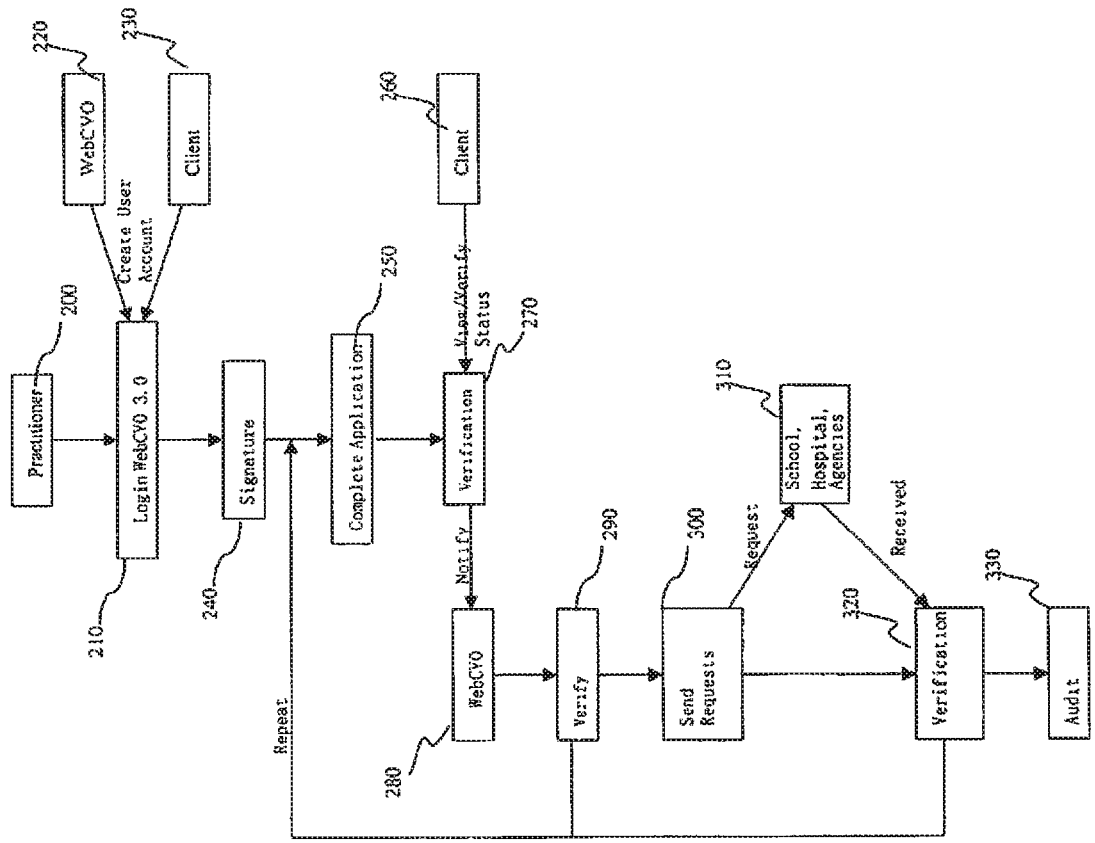
FIG. 3 graphically illustrates the logic flow of an electronic credentialing process in accordance with an exemplary embodiment of the present invention.

For example, FIG. 3 graphically illustrates the logic flow of an exemplary credentialing process. In one embodiment practitioners 200 may logon to the described exemplary electronically credentialing system 210 and view their own credentials information online. In addition, in an exemplary embodiment the organizations which collect and verify submitted credentials applications may also remotely logon to the system via a global computer network, such as, for example the Internet 220. In addition, organizations that outsource this responsibility to another organization such as for example, health plans, health systems, hospitals, managed services organizations, preferred provider organizations, medical groups, and independent practice associations may also be provided remote access to the described exemplary system 230.

The described exemplary system may grant different types of users varying degrees of access to the WebCVO system. In one embodiment the described exemplary system may utilize assigned login IDs and passwords to redirect users to different web pages for different functionalities. In addition, an exemplary system may sign each practitioner record with an electronic signature 240. This signature may be captured either through electronic creation by the practitioner or by the scanning of a practitioner's actual signature.

An exemplary system may require practitioners to complete all mandatory data fields before submitting a credentials application for verification 250. An exemplary embodiment of the present invention allows for the assigning of required data fields by practitioner type and verification phase. For example, in one embodiment practitioners may be required to complete a set of data fields pertinent to their field of practice. Practitioners may also be required to complete an initial set of data fields (also pertinent to their field of practice) and upon satisfactory verification of those fields, the practitioner may then be required to complete a secondary, tertiary, etc. set of data fields. In accordance with an exemplary embodiment the required fields are assigned when a practitioner's record is created.

In addition, for applications submitted online, the organization performing credentials verification may view the application and approve it for verification initiation 260. In practice the described exemplary system may automatically initiate the verification process 270 for submitted applications that are approved for verification 280.

The described exemplary system may retrieve electronic data from primary source verification websites 290. The described exemplary system may send requests to non-electronic data sources via email, letter or fax, (or phone) including a copy of a release from the corresponding practitioner with electronic signature and delineation of privileges, if desired 300.

An exemplary system may correlate the verification information received from external sources with the credentials information entered by the applicant. The described exemplary system may auto-update the database for matched data. In addition, in one embodiment the described exemplary system may attempt to identify reasons for a mismatch between the verification data received from external sources and the credentials information entered by the applicant.

For example, the system may electronically or manually attempt to identify clerical errors, such as typographical errors that may occur during the conversion of a scanned document to text by an optical character recognition program. The system may then request that the applicant provide an explanation for any data mismatches that cannot be attributed to errors in the data entry or correlation process. An exemplary system may then verify newly entered data by correlating it with the verification information received from the external sources.

In one embodiment, the system may automatically track the receipt of verification information and may automatically re-send verification requests if information is not received. In an exemplary embodiment, time frame intervals for the re-sending of verification requests are determined by the verifying organization. Further, non-responsive sources may be routed to an electronic tickler program for distribution to and follow up by credentials staff.

Non-electronic data sources may return requested verifications through email, fax, letter or the like 310. The described exemplary system may route information received from non-electronic sources to an electronic work tickler for distribution to and verification by credentials staff 320. Alternatively, if the verification information is received via teleform it may be auto updated to the database.

In addition, an exemplary system may route mismatched data as well as matched data to an electronic tickler for distribution to and manual verification by credentials staff 290. In addition, in one embodiment, the described exemplary system may route practitioner information to an audit program to confirm verification was performed correctly 330. The described exemplary system may utilize a single, double or triple audit process.

Figure 4:
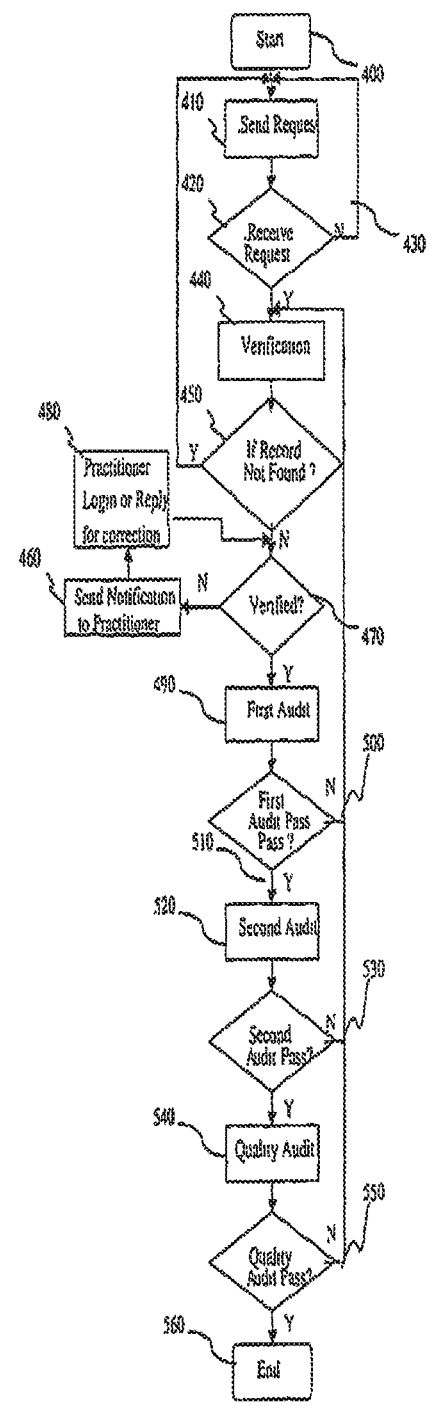
FIG. 4 is a flow chart illustrating an audit process for the verification of credentials information in accordance with an exemplary embodiment of the present invention.

For example, FIG. 4 graphically illustrates an exemplary triple audit process. In operation, the described exemplary system may manually or automatically send requests to verifying sources 410 in response to a verification request from a credentialing organization 400. In one embodiment the system may mark information received in response to verification requests for verification 420. Otherwise the system may automatically send another request to the verifying sources in accordance with preset time intervals until the requested verification information is received 430. If a response to the request is not received the system may route the information to an electronic work distribution and reminder program for processing by the credentialing organization.

In practice the credentialing organization or the WebCVO verifies information received from the verifying source 440. If a verifying source responds with a "Record Not Found" response 450, the described exemplary system may notify the practitioner via email, fax or letter 460 and ask for corrected information. The practitioner may then respond with corrected information 480 and the system may then send another request to the verifying source 410 with corrected information.

The described exemplary system may route verified credentialing information to an electronic work distribution program for auditor review 490. In one embodiment, the auditor reviews the verification information received to ensure that it matches that reported on the practitioner's credentials application. If the verification information received matches that reported by the practitioner, the auditor marks the audit as "Pass." In the event the verification information received does not match that reported by the practitioner, the auditor marks the audit as "Fail."

Should the auditor mark the first audit as failed 500, the original verification is archived and the verification and audit processes are re-initiated. Should the auditor mark the first audit as passed 510, credentialing information is routed to an electronic work tickler for second auditor review 520. Should the auditor mark the second audit as failed 530, the original verification is archived and the verification and audit processes are re-initiated.

In one embodiment, the system may route information that passes two consecutive verification audits to an electronic work distribution program for quality audit review of all verifications 540. Should the auditor mark the quality audit as failed 550, the original verification is archived and the verification and audit processes are re-initiated, otherwise the verification audit has been successfully completed 560.

The described exemplary electronic credentials verification system preferably supports a plurality of data methods of credentials information input. For example, in one embodiment an applicant may enter credentials information from a global computer network such as, for example, the Internet. Alternatively, credentials information may also be imported from a variety of sources such as, for example, a CD-ROM, teleform that is scanned in using optical character recognition, etc. In an exemplary embodiment, the system may require the applicant to provide complete information by continually contacting the applicant via email, fax, letter or a combination thereof until all information is complete.

Figure 5:
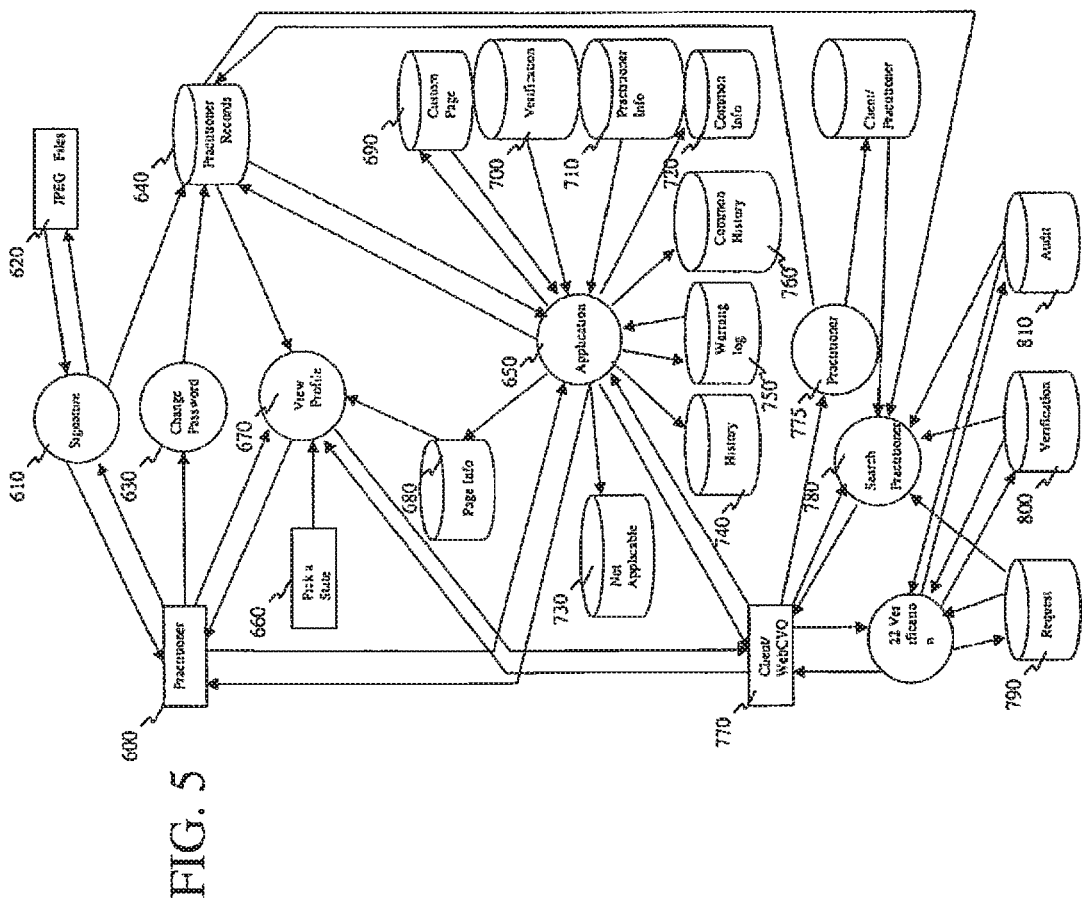
FIG. 5 graphically illustrates an online electronic verification process in accordance with an exemplary embodiment of the present invention.

FIG. 5 graphically illustrates an exemplary online credentials application process. For online application submissions, the described exemplary system may automatically or manually assign a login ID and password to a practitioner 600 for system access. In an exemplary process, a practitioner must review and accept an information release agreement and create a signature 610 after logon to the system. The described exemplary system may capture a scanned signature or an electronic signature for each practitioner and may digitally convert the captured signature to a globally unique identifier (GUID). In one embodiment, a scanned in signature may be saved in JPEG format 620.

In an exemplary embodiment, the system records the user identification and date and time for each piece of data entered and any and all subsequent changes to provide a complete audit trail for credentials information entered into the system. In this manner, the system transforms a practitioner's credentials application from a static record into a dynamic, real-time comprehensive record that may be linked to enterprise-wide databases to capture or supplement other practitioner data.

In one embodiment, the system may prompt the practitioner to change his or her password 630 and may create a practitioner record by selecting from a set of required data fields that are pertinent to the practitioner's field of practice as well as an initial set of required data fields (also known as a pre-application). When the pre-application is verified an exemplary system may require the practitioner to complete a secondary, tertiary, etc. set of required data fields. An exemplary embodiment of the present invention may also support the creation of practitioner records having additional data fields that are not included in the standard applications stored in the credentials information applications repository 650.

In the described exemplary embodiment, a practitioner may select credentials applications by state from the application library 660. In one embodiment, a practitioner may retrieve and view the selected credentials application 670 which is populated with the specific information entered by the practitioner 680.

The credentials application 650 may comprise a variety of user defined custom pages 690, the results of the verification processes 700, as well as additional practitioner data input through modification 710. An exemplary credentials application may further comprise common data information 720 such as information received from insurance carriers, schools, hospitals, government agencies, etc. The application may also include pages (tabs) that may be marked as not applicable to the particular practitioner 730, as well as archived data 740, a warning log comprised of data mismatches and identified adverse actions 750 and common field level history tracking data 760.

In one embodiment the application may be composed of elements that conform to a standardized programming language such as, for example, the extensible markup language (XML) specification. As is known in the art, XML is a markup language for documents containing structured information. Structured information contains both content (words, pictures, etc.) and some indication of what function that content performs. The utilization of a standardized programming language further promotes the automatic utilization of the credentials information across enterprise-wide databases to capture or supplement other practitioner data In one embodiment organizations 770 may have access to practitioner applications 775 and practitioner 775 records 640. An organization may also search practitioners in the system 780 to retrieve and review requested information 790, verification information 800 and audit information 810. Organizations may also access practitioner verification information to view the status and detailed information 820.

Figure 6:
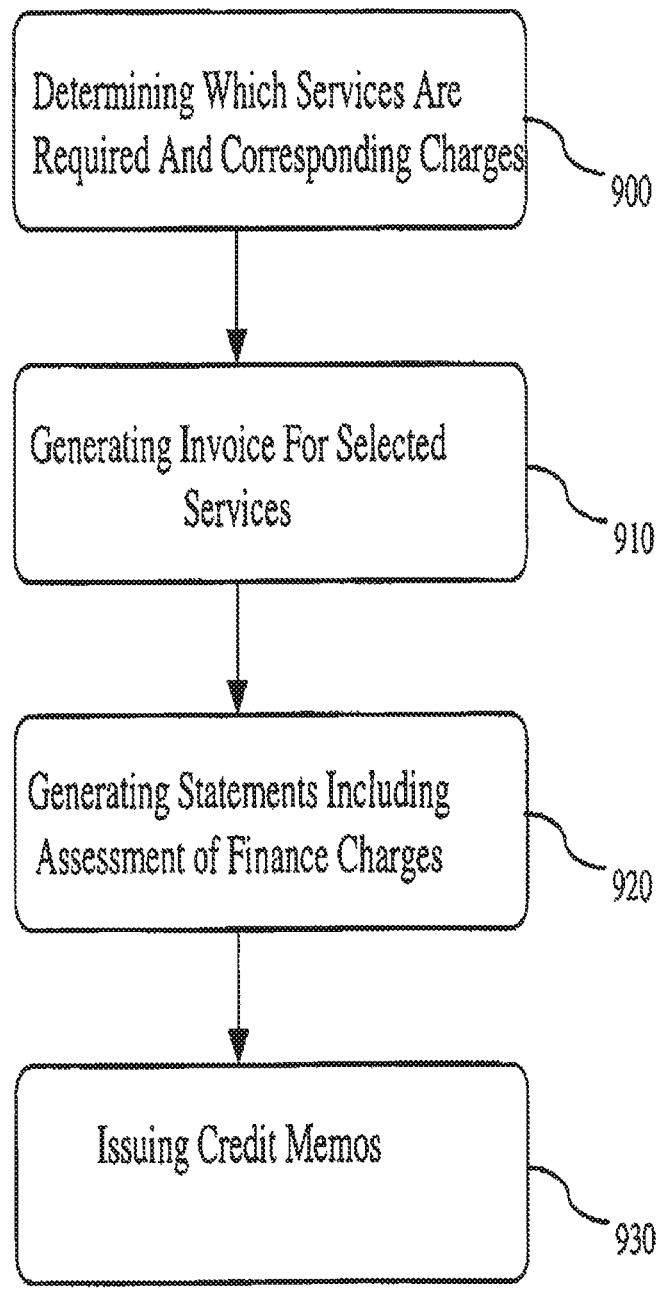
FIG. 6 graphically illustrates a process for creating and maintaining accounting records associated with the verification of credentials information in accordance with an exemplary embodiment of the present invention.

Referring to FIG. 6, an exemplary embodiment of the present invention may create and maintain accounting records associated with the verification of credentials information. For example, the described exemplary system may determine which services are required for a particular client as well as the charges associated with those services 900. The described exemplary embodiment may then automatically generate an invoice for the appropriate services when they are performed. 910. The system may also generate accounting statements in accordance with the appropriate services including assessments of finance charges where appropriate 920. The system may then automatically issue credit memos 930 from the accounting statements 930.

Figure 7:
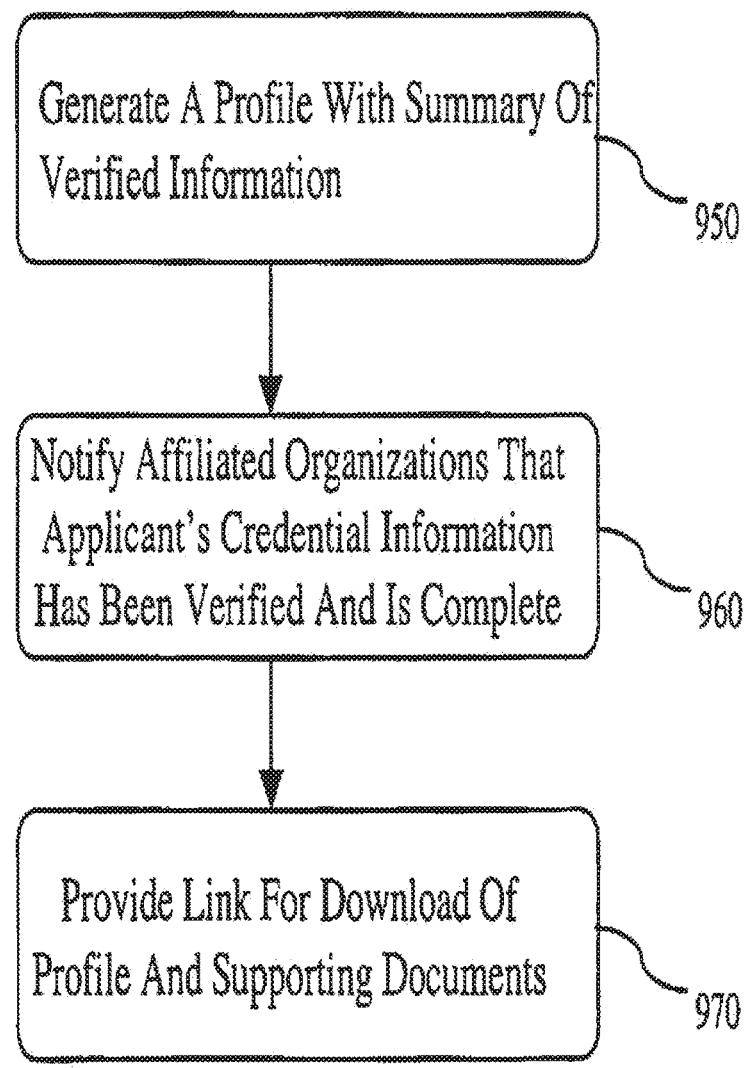
FIG. 7 graphically illustrates a process for generating verified credentials profile information including copies of records from external sources in accordance with an exemplary embodiment of the present invention.

Referring to FIG. 7, an exemplary embodiment of the present invention may also generate verified credentials profile information including copies of all records from external sources. For example, in one embodiment, the described exemplary system may generate a profile with a synopsis of verified information as required by regulatory agencies within the field of practice of the applicant 950. The describe exemplary system may also notify affiliated organizations that the applicant's credentials information has been verified or re-verified and is complete. The system may also provide a hyperlink 970 to a site from which interested parties may download the verified credentials profile. The system may further make copies of the electronic and scanned documents utilized in the verification process available for download as well.

Figure 8:
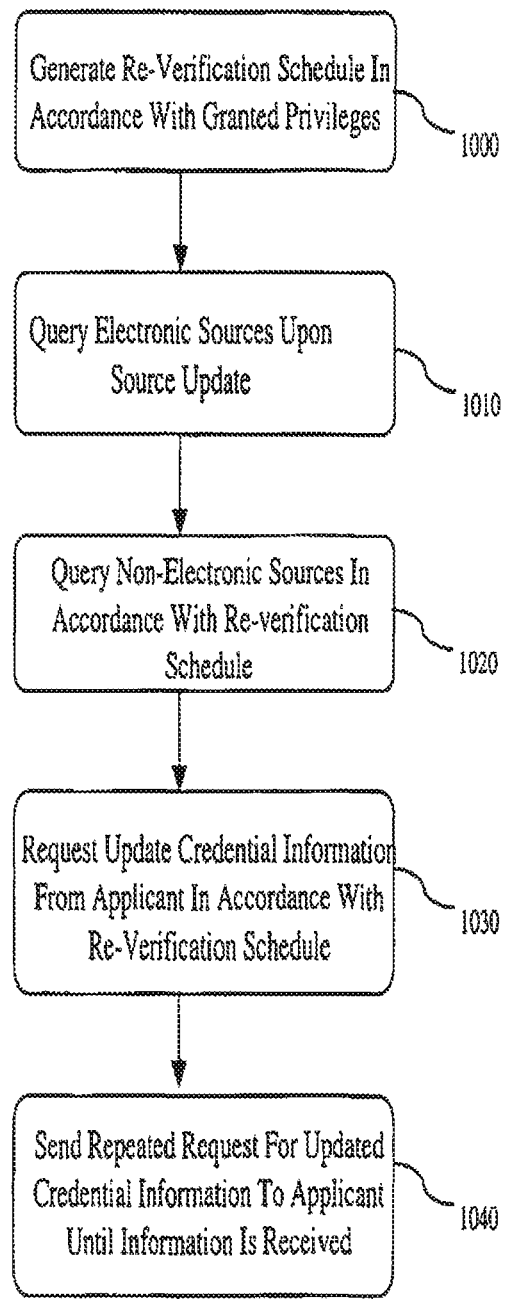
FIG. 8 graphically illustrates a process for creating and maintaining a continuous calendar of re-verification of an applicant's credentials in accordance with an exemplary embodiment of the present invention.

Referring to FIG. 8 an exemplary embodiment of the present invention may also create and maintain a continuous calendar of re-verification of an applicant's credentials information. For example, an exemplary system may create a re-verification schedule in accordance with the requirements for re-verification for a particular set of privileges 1000. The described exemplary system may then query electronic sources 1010 and non-electronic sources in accordance with the prescribed schedule 1020. The described exemplary system may also request that the applicant update credentials information on a prescribed schedule 1030 and continually send repeated requests for updated information until the requested information is received 1040.

Figure 9:
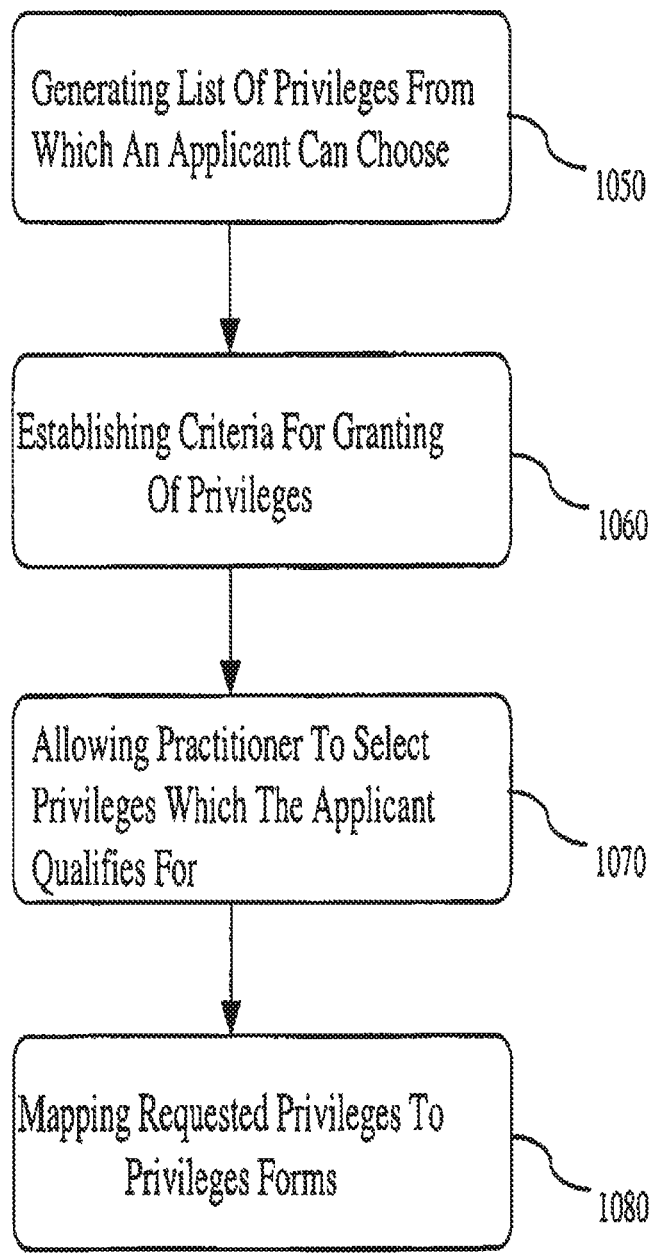
FIG. 9 graphically illustrates a process for allowing applicants to request privileges based upon analysis of credentials information in accordance with an exemplary embodiment of the present invention.

Referring to FIG. 9 an exemplary embodiment of the present invention may also allow applicants to request privileges based upon analysis of credentials information. For example an exemplary system may generate a list of privileges from which a practitioner in a particular field may select 1050. The described exemplary system may then establish criteria such as, for example, level of education, training and experience for the granting of each privilege 1060. The system may then compare the applicant's credentials with the required criteria and restrict the privileges which the applicant may select from to those for which the applicant has satisfied the specified criteria 1070. The system may then map the requested privileges to appropriate privileges forms 1080 which may then be automatically sent via email, fax or letter to external sources for review of competence.

In an online system, a "pop up" message may be generated when an applicant attempts to select a privilege which the applicant does not qualify for. The pop message may provide the reasons for privilege ineligibility. Alternatively, an exemplary system may auto-generate an email, fax or letter to the applicant that provides the reasons for privilege(s) ineligibility.

Figure 10:
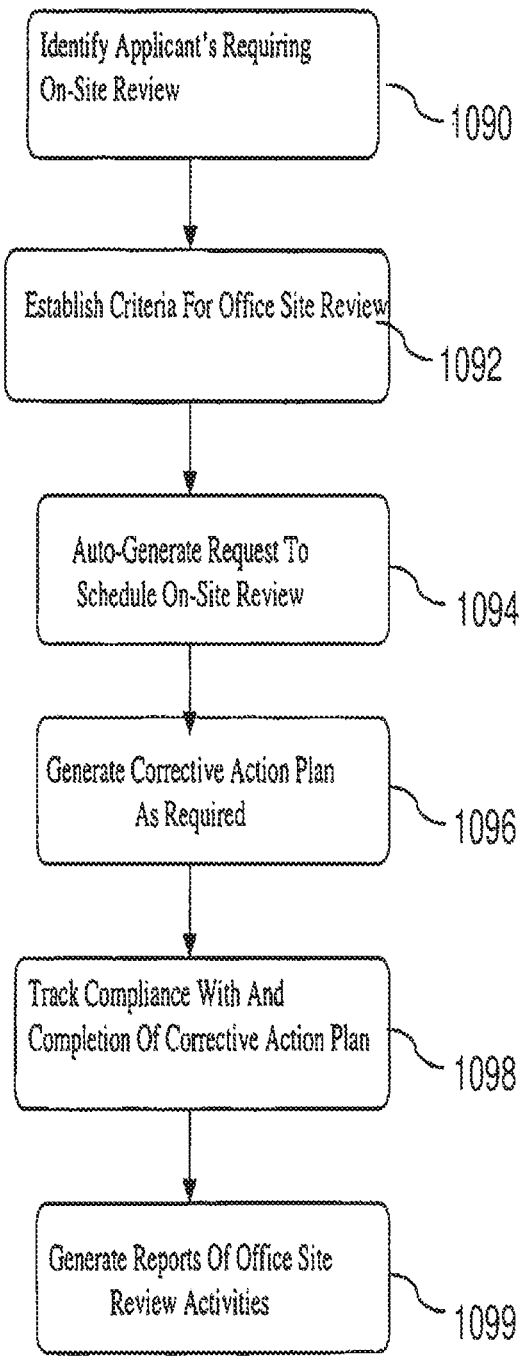
FIG. 10 graphically illustrates a process for reviewing select practitioner office sites in accordance with an exemplary embodiment of the present invention.

Referring to FIG. 10, an exemplary embodiment of the present invention may also allow for the review of select practitioner office sites. For example, in one embodiment an exemplary system may identify practitioners requiring office site review to satisfy the regulatory requirements, etc. 1090. The system may then establish the criteria for the on-site review in accordance with the requirements for regulatory compliance 1092. The system may then auto-generate a request to schedule an on-site review 1094, generate review results and generate a corrective action plan, if required as a result of the review 1096. An exemplary system may track compliance with and completion of the corrective action plans 1098 and generate a report of the office site review activities 1099.

The invention described herein will itself suggest to those skilled in the various arts, alternative embodiments and solutions to other tasks and adaptations for other applications. It is the applicants' intention to cover by claims all such uses of the invention and those changes and modifications that could be made to the embodiments of the invention herein chosen for the purpose of disclosure without departing from the spirit and scope of the invention.

Data Mapping

Embodiments of the present invention are directed to a visual mapping tool for visually mapping various healthcare administrative forms to a common healthcare object model. Those forms may then be dynamically completed via a runtime form processing engine (referred to as a runtime engine) that retrieves data stored in a relational database and uses the mapping data to automatically populate corresponding fields of the forms without manual input by the user. Specifically, embodiments of the present invention are directed to a healthcare common object model linked to a relational database, a visual mapping tool that facilitates automated mapping of the healthcare common object model to healthcare administrative forms, and a generated map file that is employed to facilitate and further automate form mapping and form population processing on a large scale.

Specifically, embodiments of the present invention provide a visual mapping tool that displays the objects of the common object model as well as the fields of a form to be mapped. A user drags and drops one or more of the displayed objects into a mapping area, and drags and drops a field to which the one or more objects are to be mapped. The user also identifies a type of association between the selected objects and the field. A mapping entry is then generated in a map file to map the selected objects to the field.

A person of skill in the art should recognize that the present system and method for visual object mapping and automated forms completion provide a streamlined and transparent process for mapping, retrieving, and pre-populating forms. According to one embodiment, the visual mapping tool provides linkage between form fields and business objects without requirement of any programming from the business users. The object model and runtime engine perform dynamic read operations on the database and utilize mapped configuration files to complete specific forms without any additional manual programming. Furthermore, changes to the underlying data model typically do not necessitate additional mapping.

Figure 11:
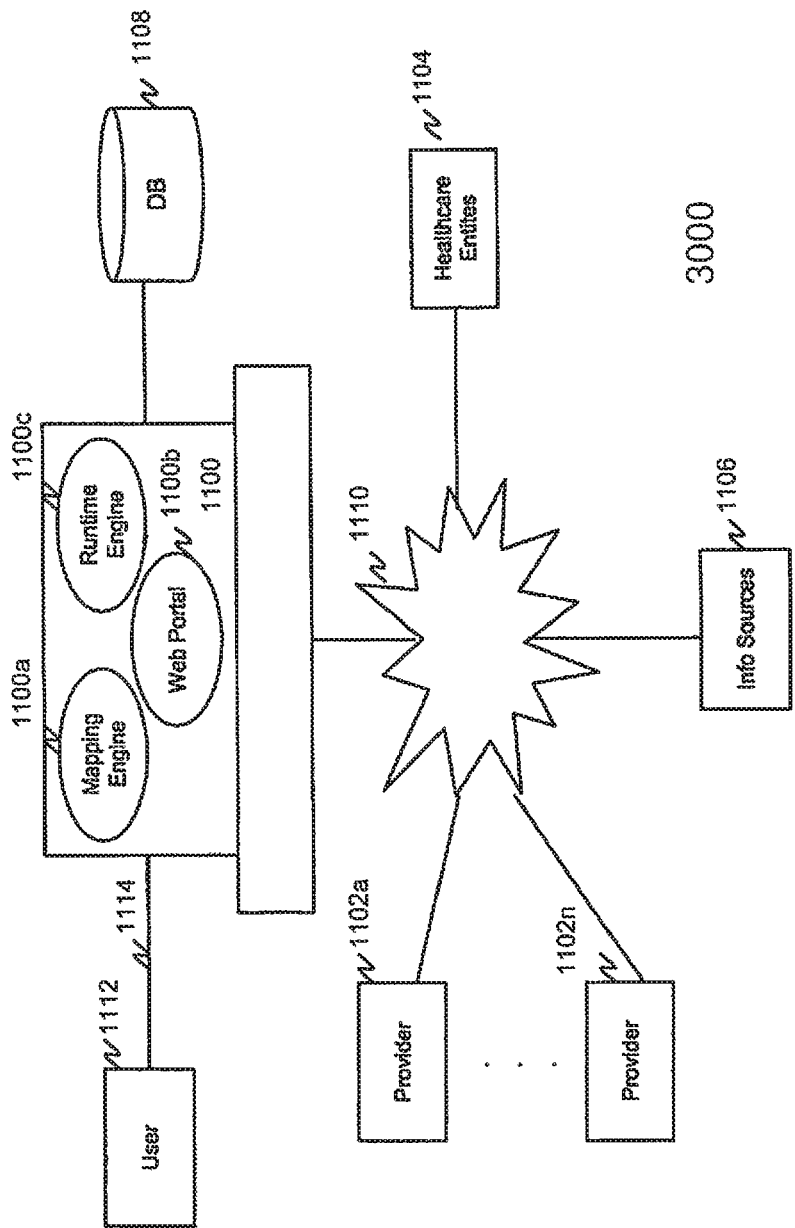
FIG. 11 is a block diagram of a system and method for visually mapping and automatically completing electronic forms according to one embodiment of the invention.

FIG. 11 is a block diagram of a system 3000 for visually mapping and automatically completing electronic forms according to one embodiment of the invention. The system 3000 includes one or more remote healthcare provider devices 1102a-1102n, healthcare entity devices 1104, and information sources 106 (collectively referred to as remote devices), coupled to one or more servers 1100 over a data communications network 1110. The communication network 1110 may be a network or combination of networks spanning any geographical area, such as a local area network, wide area network, regional network, national network, and/or global network. The Internet is an example of a current global computer network. In addition, the communication network may be a hardwire network, wireless network, or a combination of hardwire and wireless networks.

Hardwire networks may include, for example, fiber optic lines, cable lines, ISDN lines, copper lines, and the like. Wireless networks may include, for example, cellular systems, personal communications service (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

Each of the remote devices may be any processor controlled device that permits access to the communication network 1110, including terminal devices, such as personal computers, workstations, servers, clients, mini-computers, main-frame computers, laptop computers, a network of individual computers, mobile computers, palm-top computers, hand-held computers, set top boxes for a television, other types of web enabled televisions, interactive kiosks, personal digital assistants, interactive or web enabled wireless communications devices, mobile web browsers, or a combination thereof. In this regard, the remote devices include a processor, memory, and one or more input devices such as a keyboard, mouse, touch pad, joystick, pen input pad, and the like. The remote devices may also include an output device, such as a display screen and audio output. The memory included in each remote device stores computer program instructions which, when executed by the processor, causes the processor to perform certain actions mandated by the computer program instructions. Such computer program instructions may also be stored in a disk, CD, or other secondary storage device.

The server 1100 may be similar to the server described in the above-referenced U.S. Pat. No. 7,529,682. The server 1100 may be hosted by a particular healthcare entity such as, for example, an insurance company, hospital, surgical center, or the like. According to one embodiment, the server may be configured to provide the electronic credentials verification and management functionalities described in U.S. Pat. No. 7,529,682. The server 1100 is also configured to map various healthcare administrative forms to a common object model, and automatically populate those forms based on data provided by a healthcare provider or other information source. The server 1100 also hosts various web portals for access by different providers, healthcare entities, administrators, and the like. For example, a provider portal allows a provider to create and maintain his profile and credentialing data for verification, forms generation, and the like. A peer network portal allows providers to create a peer network of providers for peer referral and the like, as is described in further detail in the above-referenced U.S. Application entitled "System and Method for Peer Referencing in an Online Computer System." Administrators may access the web portal to map administrative to a common object model, respond to requests for approval of mapped forms, and the like.

In this regard, the server includes a mapping engine 1100a, one or more web portals 100b, and a runtime engine 1100c. The mapping and run-time engines and the web portals may be implemented as software modules that are executed by a processor in the server based on computer program instructions stored in memory. The mapping and run-time engines may each be a separate software module, or one or more of the engines may be combined into a single module or further divided into one more sub-modules as may be appreciated by a person of skill in the art. A person of skill in the art should also recognize that the engines may be implemented in hardware, firmware (e.g., ASIC), or a combination of hardware, firmware, and/or software.

The data storage device 1108 may be any hard disk drive or drive array which hosts a number of purpose-built databases and files useful for implementation of the system 3000. For example, the data storage device may take the form of a hard disk or disk array, storing a provider's profile, credentialing information, networking database with information on the provider's peer network, healthcare forms, map files, object model, and information of other entities associated with the system 3000. Any electronic healthcare form may be mapped and stored in the data storage device. Such exemplary forms include, but are not limited to enrollment forms, credential forms, medical claims, information forms, and the like. Of course, a person of skill in the art should recognize that the present invention is not limited to the healthcare field. Hence, the forms that are stored and mapped for auto-completion may vary depending on the field in which the present invention is utilized.

According to one embodiment of the invention, a user device 1112 is coupled to the server 1100 via a communications link 1114. The user device 1112 may be similar any of the remote devices described above. The communications link 1114 may be a direct wire, an infrared data port, a wireless communications link, global communications link such as the Internet, or any other communications medium known in the art.

According to one embodiment, the user device 1112 accesses the mapping engine 1100a hosted by the server 1100 for mapping various healthcare forms to a common object model, such as, for example, a healthcare object model, as described in further detail below. The access may be via a graphical user interface (GUI) provided, for example, by the mapping engine 1100a or some other user interface engine. Alternatively, the access may be via the web portal 1100b accessed over the Internet. The user device 1112 may also access an administrative portal for approving a map file generated upon mapping of a particular form, as well as to engage in different administrative functions. The administrative portal may be provided as part of the web portal 1100b for access over the Internet. A user accessing the user device 1112 may be, for example, a provider, healthcare entity, administrator, or anyone with authority to create or edit a map file.

According to one embodiment of the invention, the mapping engine 1100 provides a visual mapping tool to enable detailed mapping between a common healthcare business object model to field objects contained in various electronic forms (e.g., PDF, XPS, Word template, web page, and the like). The mapping tool may provide one or more graphical user interface screens for guiding a user through the mapping process, and may identify a specific type and version of the form to the mapped, the fields in the form, and the relationships to each object in the healthcare object model. According to one embodiment, the common object model represents real life entities, e.g., provider practice types, licenses, certifications, etc. Thus, the intended mapping user can easily follow the object structure and drag-and-drop each object, attribute, and/or property (collectively referred to as an object) for a corresponding field object of the form being mapped, via the graphical user interface. Each completed mapping process produces a structured map file in XML or other standard format with detailed metadata that stores a reference to the specific form that was mapped. The map file and related metadata is then stored in the data storage device 1108.

Figure 12:
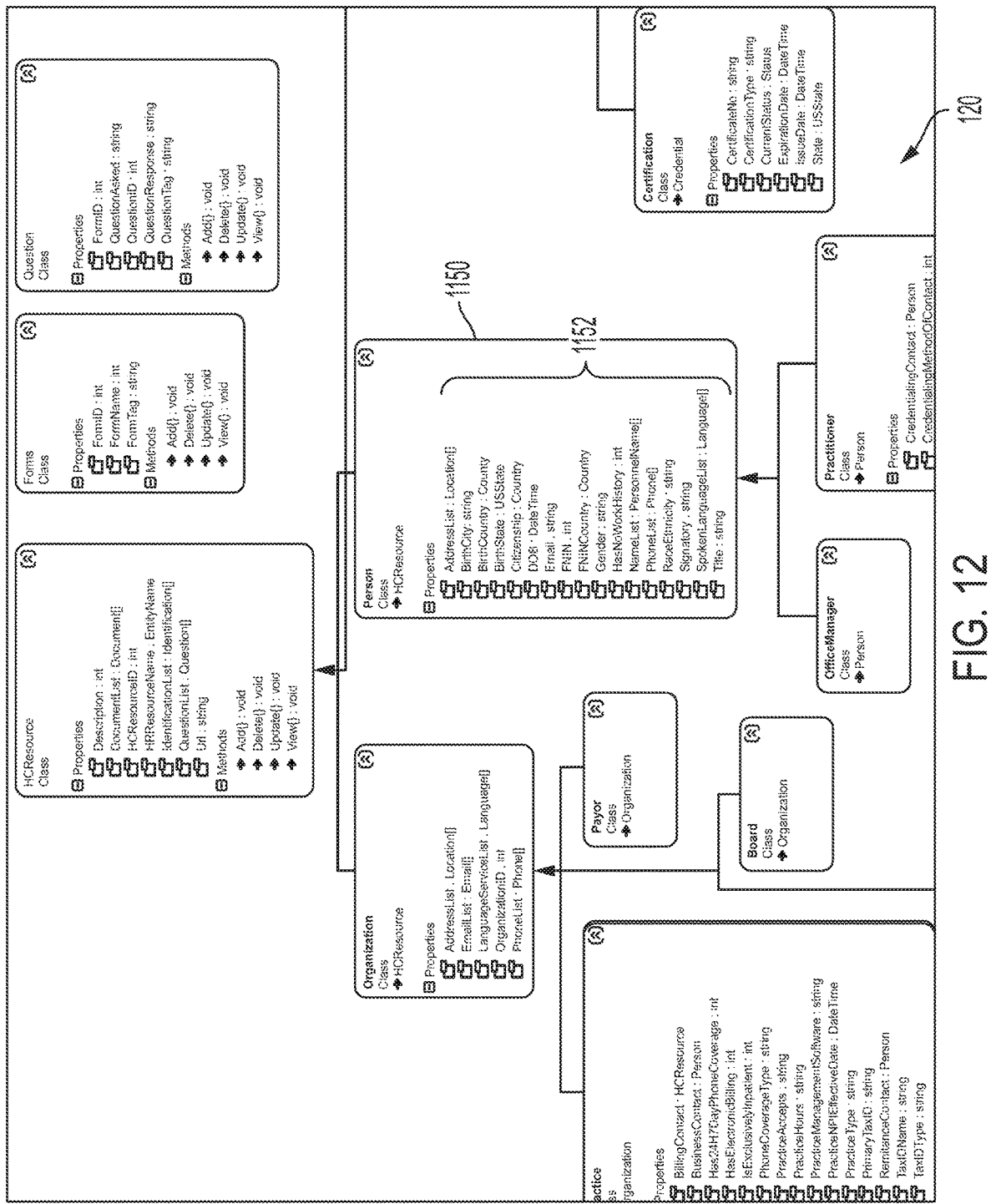
FIG. 12 is a schematic layout diagram of an exemplary common healthcare class object model according to one embodiment of the invention.

FIG. 12 is a schematic layout diagram of an exemplary common healthcare class object model 120. According to one embodiment, the model is organized around common administrative processes, although other types of organization formats will be readily apparent to a person of skill in the art. General healthcare entity information (e.g., doctors, providers, healthcare organizations, insurance companies, hospitals, license, address, affiliations, etc.) are represented as classes/objects 1150. The detailed information for each entity is represented by the object's attributes/properties 1152. The relationships of these entities are captured with HL-7 compliant relations. The common class object model can in turn dynamically generate a data access layer that may be accessed to create, read, update, and delete (CRUD) information stored with respect to the object model, upon request, via conventional mechanisms known in the art.

According to one embodiment of the invention the runtime engine 1100c retrieves a specific map file as soon as a system or user requests auto completion of any form selected from a pre-mapped form library. The runtime engine is configured to retrieve the exact map file for the selected form using the metadata and unique identifier associated with the map file. An execution component of the runtime engine uses the metadata and map file to derive form fields and corresponding instances of each related object, and instantiates the data access layer for dynamic data retrieval from the common object model.

Figure 13:
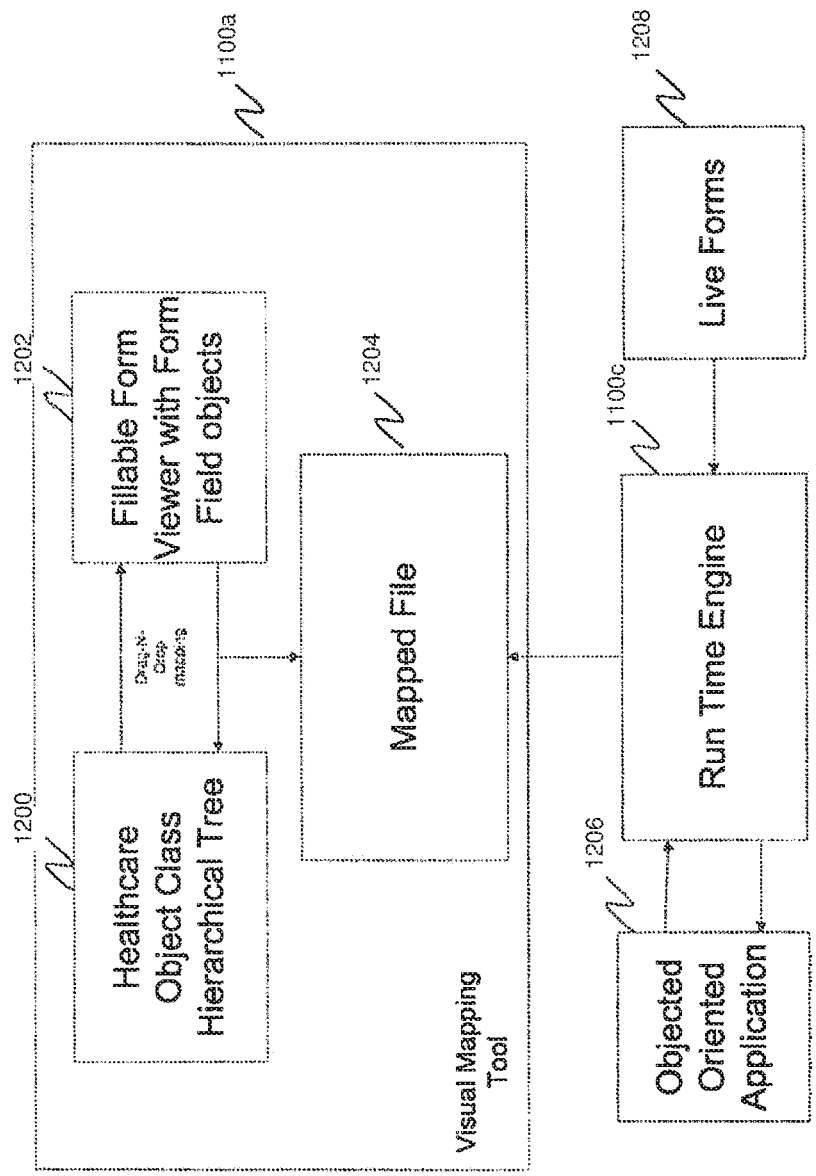
FIG. 13 is a functional block diagram of a mapping engine and a runtime engine according to one embodiment of the invention.

FIG. 13 is a functional block diagram of the mapping engine 1100a and the runtime engine 1100c according to one embodiment of the invention. The mapping engine 1100a visually displays a hierarchical tree 1200 representative of a healthcare object class on a display coupled to a remote device, such as, for example, on the user device 1112. The mapping engine further displays on the device a form to be mapped to the object class. As the mapping user invokes a mouse, keyboard, keypad, etc., of his or her user device 1112 to drag and drop model objects to map to corresponding field objects in the displayed form, associations are formed between the objects and the form fields. The association is stored in a map file 1204, which in turn is stored in the data storage device.

When a healthcare provider submits a request to generate a form, such as, for example, via the provider device 1102, which submits the request via the web portal 1100b, the request is forwarded to the runtime engine 1100c. The runtime engine 1100c retrieves the requested form 1208 from a database of forms stored in the data storage device 1108. The runtime engine further invokes an object oriented application 1206 that accesses the data access layer of the common object model to retrieve data stored for the provider according to the object model, and further uses the map file 1204 for the requested form 1208 to automatically populate the fields of the form. For example, the data to be automatically populated on the form may be the provider's credentialing data, which the provider may have already provided for filling out a different form.

Figure 14:
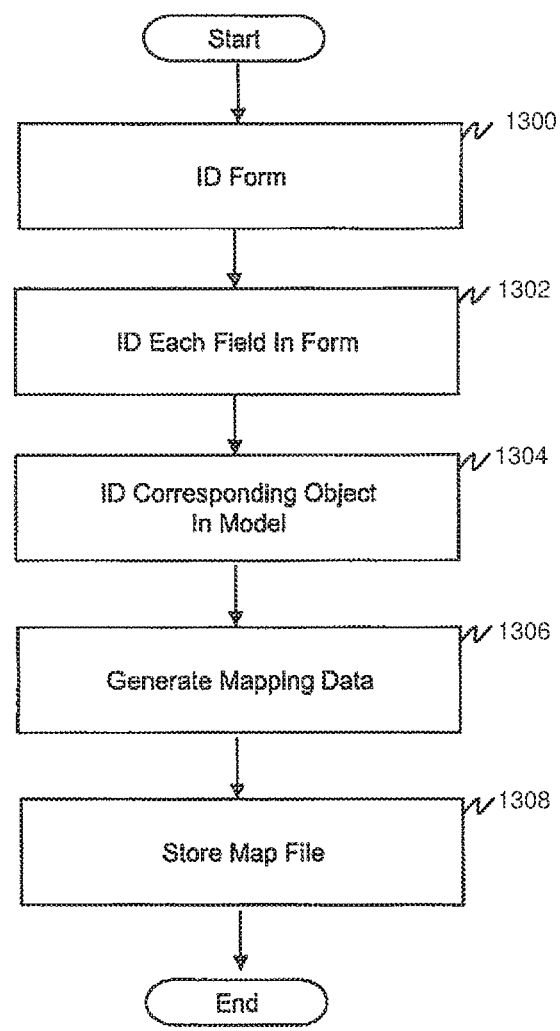
FIG. 14 is a flow diagram of a process executed by a mapping engine to generate a map file according to one embodiment of the invention.

FIG. 14 is a flow diagram of a process executed by the mapping engine 1100a to generate a map file according to one embodiment of the invention. The process may be described in terms of a software routine executed by the processor in the server 1100 based on instructions stored in the server's memory. A person of skill in the art should recognize, however, that the routine may be executed via hardware, firmware (e.g., via an ASIC), or in any combination of software, firmware, and/or hardware. Furthermore, the sequence of steps of the process is not fixed, but can be altered into any desired sequence as recognized by a person of skill in the art.

Figure 18:
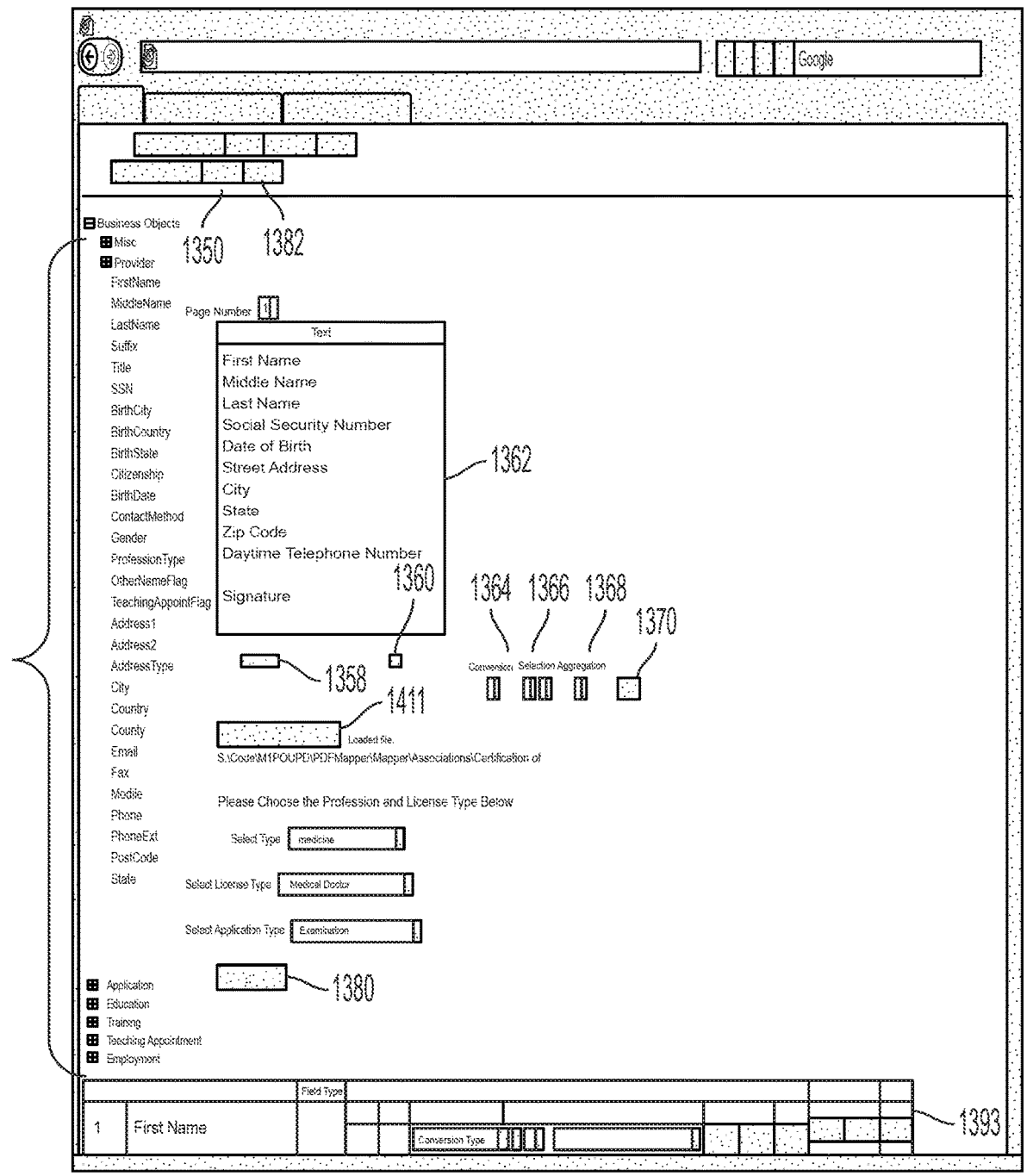
FIG. 18 is screen shot of an exemplary screen for mapping objects of a common object model to fields of a form, according to one embodiment of the invention.

In step 1300, the mapping engine 1100a receives identification of a form to be mapped. In this regard, the mapping engine invokes a GUI to display a GUI screen on the user device 1112, such as the GUI screen depicted in FIG. 18. The GUI screen of FIG. 18 provides, a browse button 1150 which, upon selection, displays a list of forms stored in the forms database of the data storage device 108. According to one embodiment, a most recent version of each form is displayed upon selection of the browse button. Alternatively, all versions of the forms may be displayed. The forms may be organized in the forms database according to any category, such as, for example, health plans, types of forms (e.g. enrollment, credential, claim, information, etc.), and the like. Each form may be associated with a status indicating whether the form has been mapped, awaiting approval of mapped data, and the like. According to one embodiment, each form is stored in a data storage device along 1108 with a unique form ID. In addition, each form is further associated with an encoding file, such as, for example, an XML, file, identifying the various field names along with their unique field IDs.

Selection of a particular form from the forms list and selecting an analyze button 1382 retrieves the encoding file containing all the fields of the form, and causes the fields to be displayed in a field list area 1362 of the display. In addition, a form viewer is invoked for displaying the selected form is a second portion of the same display, or alternatively, on a separate window. FIG. 19 is a screen shot of an exemplary screen/window 1352 displaying a form that has been selected for mapping. According to one embodiment of the invention, the form includes one or more tillable fields 1354a-1354e, each of which is associated with a unique field ID, as identified in the corresponding encoding file.

The relevant object(s) from the common class object model 120 is displayed by the GUI as a hierarchical object tree 1356 (which is similar to the hierarchical tree of FIG. 13). One or more attributes and properties associated with the particular object may be collapsed from view until selected by the mapping user.

In step 1302, the mapping engine 1100a identifies, based on input provided by the user, the fields in the displayed form. In step 1304, the mapping engine further identifies, based on input provided by the user, the attributes and properties that are to be mapped to the identified fields, from the displayed hierarchical tree. In step 1306, the mapping engine generates a map file with the mapping data, and stores the map file in the data storage device in step 1308. Thus, unlike the prior art requiring manual coding of each form to create a one-to-one mapping of a form field directly into a database field, the present invention provides a single common object model that may be reused for various forms to automate and facilitate the mapping process.

According to one embodiment of the invention, the mapping of objects of the model to fields of a form is accomplished by dragging and dropping the objects and the fields into a predefined mapping area so as to cause an association between the objects and fields in the area. Alternatively, the mapping may be accomplished by dragging and dropping the displayed objects to corresponding fields of the displayed form, or vice versa. In yet another embodiment, other visual mechanisms for identifying objects and fields to be mapped to one another may be provided by the GUI instead of the drag-and-drop mechanism, such as, for example, highlighting the objects and fields that are to be mapped.

According to the embodiment displayed in FIG. 18, a field from the field list area 1362 is selected, dragged, and dropped into a field ID portion 1358 of a mapping area provided by the GUI. Similarly, one or more corresponding business objects from the object tree 1365 are selected, dragged, and dropped into a business object portion 1360 of the mapping area to cause the mapping of the selected form field with the selected business object(s).

If multiple data entries are stored for a particular business object, a selection/row# option 1366 may be selected to indicate the data entry that is to be selected for pre-populating the form. For example, multiple telephone numbers may be stored in multiple rows for a "Phone" business object. A user may indicate via the selection/row# option 1366 the row storing the telephone number that is to be used for purposes of pre-populating the form.

In addition, a user may define the type of association or mapping to be made between a form field and object(s) appearing in the mapping area. According to one embodiment of the invention, the association or mapping may default to be a one-to-one connection. However, more complex associations may be selected by the user, such as for example, a particular type of conversion (also referred to as derivation or transformation) from conversion drop down list 1364, or a particular type of aggregation from an aggregation drop down list 1368. For example, the user may select a connector from the conversion drop down list 1364 that indicates a derived association that may be defined by one or more functions.

In the event a derived association is selected, the mapping engine is configured to prompt for information that is needed for deriving a value to be filled into one or more field(s) of the form, based on corresponding information in the object model. As an example, a user may indicate a derived association for a gender object where the model requires the gender value to be "male" or "female." However, in the corresponding gender field of the form being mapped, the acceptable values may be "1" for male and "2" for female. In indicating that the association for the gender object is a derived association, the user specifies that "male" should be converted to a value of "1," and that "female" should be converted to a value of "2," when pre-populating this particular field of the form.

The selected connector may also identify a transformation rule for transforming an aspect of the stored values. For example, the transformation rule may be to always capitalize the first letter of the value when pre-populating the corresponding field, or perform some other transformation in the formatting of the data being entered into the form. For example, data may have to be truncated if it exceeds the size of a field to which it is being inserted.

Figure 20:
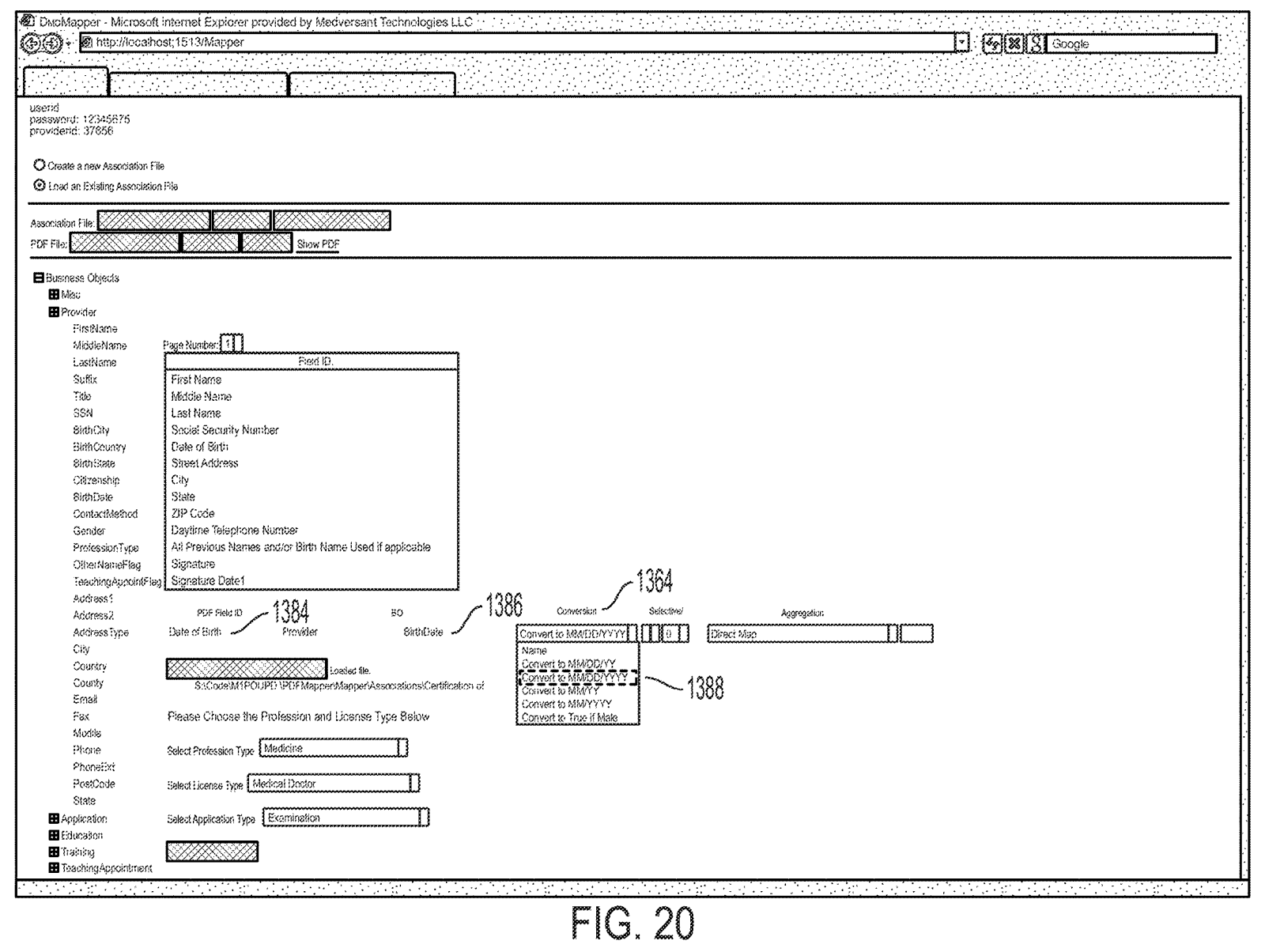

FIG. 20 is a screen shot of an exemplary screen with a list of conversion options in the conversion drop down list 1364.

According to one embodiment, conversions, derivations, and transformations are all simply referred to as conversions. In the screen shot of FIG. 20, the user has indicated that a date of birth field 1384 of the form is to be mapped to a provider's birth date object 1386. The user further has indicated that the type of mapping is a specific type of conversion of the business object data by selecting a conversion rule 1388 from the conversion drop down list 1364. The selected conversion rule 388 instructs the running engine 1100c that when populating the date of birth field in the form with the birth date data stored in the common object model, the running engine 1100c is to invoke a set of associated computer instructions for running an algorithm that converts the stored data into a MM/DD/YYYY format before populating the field, if not already in this form in the database. Such an algorithm will be apparent to a person of skill in the art.

Referring again to FIG. 18 if multiple objects have been selected from the object tree 1356 for mapping into a single from field, the user may select a particular type of aggregation rule from an aggregation drop down list 1368. According to one embodiment of the invention, the aggregation rule controls how the data aggregated from the different objects are to be joined and displayed on the mapped field when it is time to populate this field.

Figure 21:
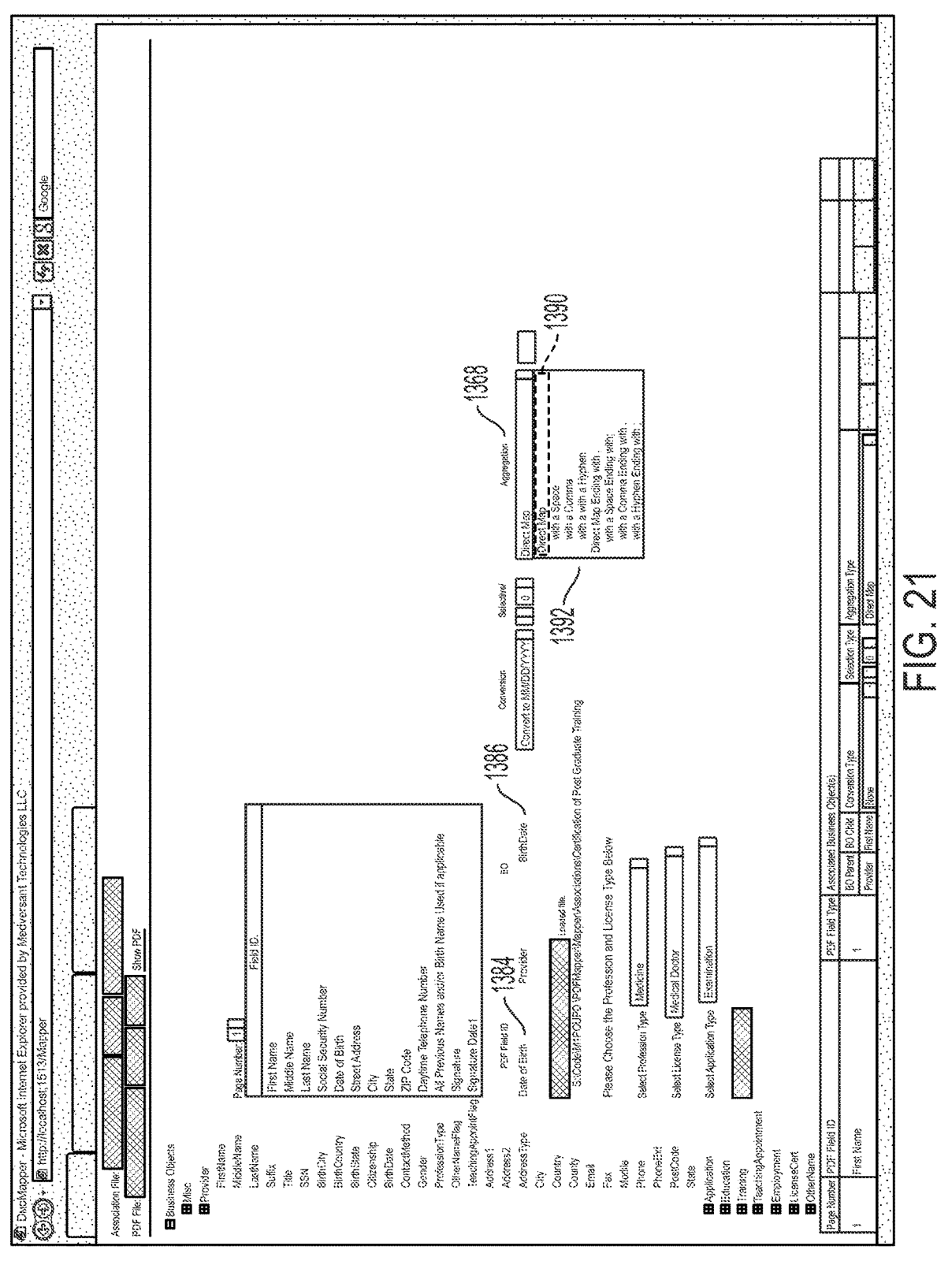

FIG. 21 is a screen shot of an exemplary screen with a list of aggregation options in the aggregation drop down list 1368. In the example provided, the user has indicated a direct mapping 1390 of the data stored for the provider's birth data object 1386 and the date of birth field 1384 of the form. However, if multiple business objects are to be mapped to a single form field, the user may select another type of aggregation mapping provided by the drop down list 1368. For example, the name field of a particular form may require that the first and last names be entered together into the same field, separated by a comma. In this case, the user selects the first name and last name objects from the object tree, and further selects the appropriate aggregation rule 1392 from the aggregation drop down list 1368 indicating how the aggregated data from the two business objects are to be displayed in the mapped field. In the example, the selected aggregation rule 1392 instructs the running engine 1100c that when populating the name field of the form with the first and last name data stored in the common object model, the running engine 1100c is to invoke a set of associated computer instructions for running an algorithm that concatenates the first and last names, with a comma in between. Such an algorithm will be apparent to a person of skill in the art.

According to one embodiment of the invention, at least the field ID portion 1358 and business object portion 1360 provided by the GUI is referred to as a mapping area. According to one embodiment of the invention, the mapping area may also include the selection/row# option 1366, conversion drop down list 1364, and aggregation drop down list 368.

Figure 22:
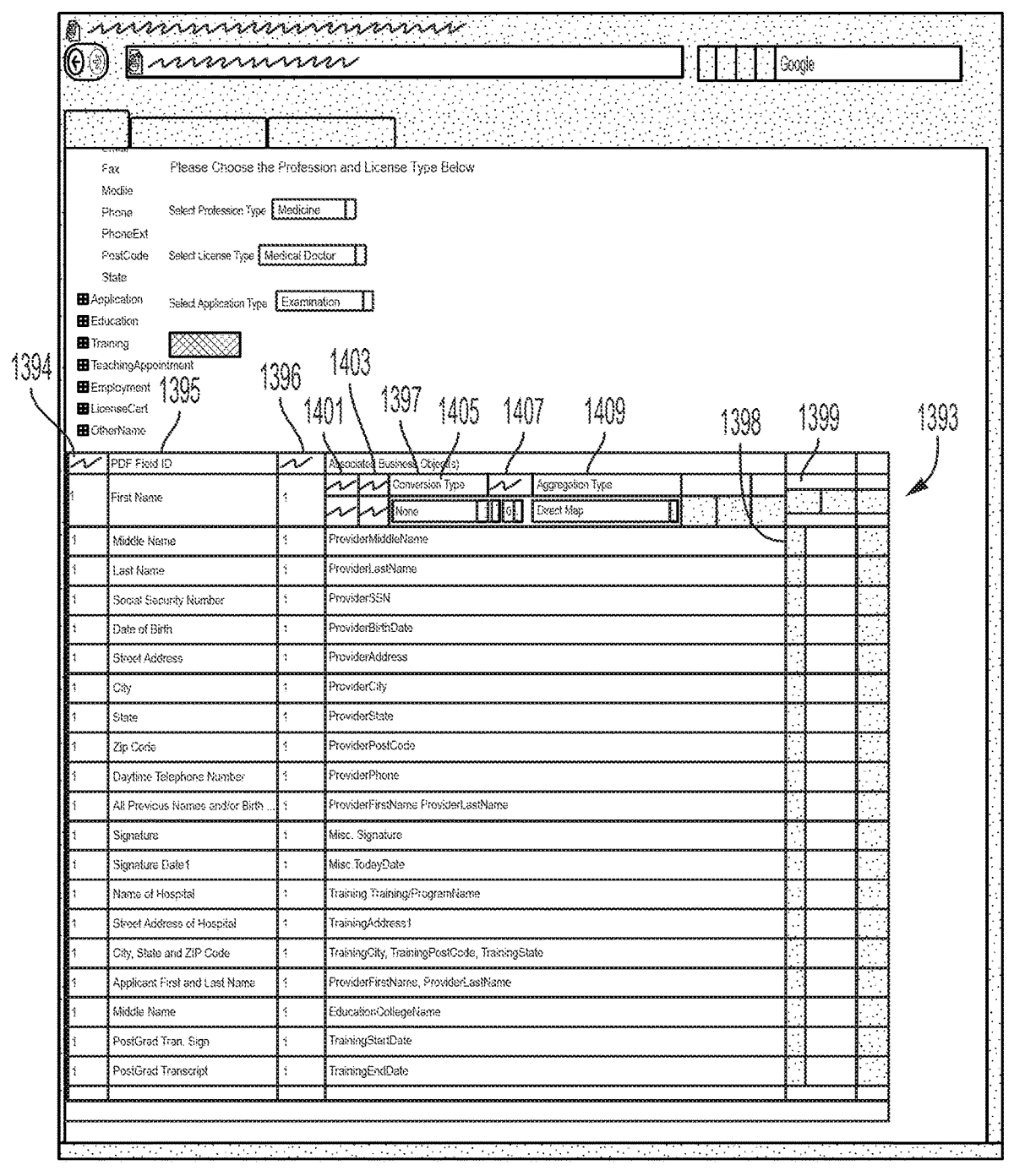

Referring again to FIG. 18, selecting a save button 1370 causes the generating of a mapping entry in a mapping table 1393 for storing the mapping information. A more detailed screen shot of an exemplary mapping table is depicted in FIG. 22. According to one embodiment, each entry of the mapping table identifies the current mapping schema including a page number 1394 of the form that was mapped, and the field ID 1395 and field types 1396 mapped for each page. The field ID may indicate the name of the mapped field. The field type may indicate the type designation of the field, such as, for example, numbers indicating whether the field is a textbox, multiple choice, checkbox, dropdown, or the like. Each entry also identifies one or more business objects 1397 mapped to each field ID. Selection of an edit button 1398 displays detailed information of the mapped business object(s), such as for example, identification of the current parent 1401 and child 1403 objects, current conversion type 1405, current selection type 1407, and current aggregation type 1409, with an option to update 1399 the current mapping information.

Figure 23:
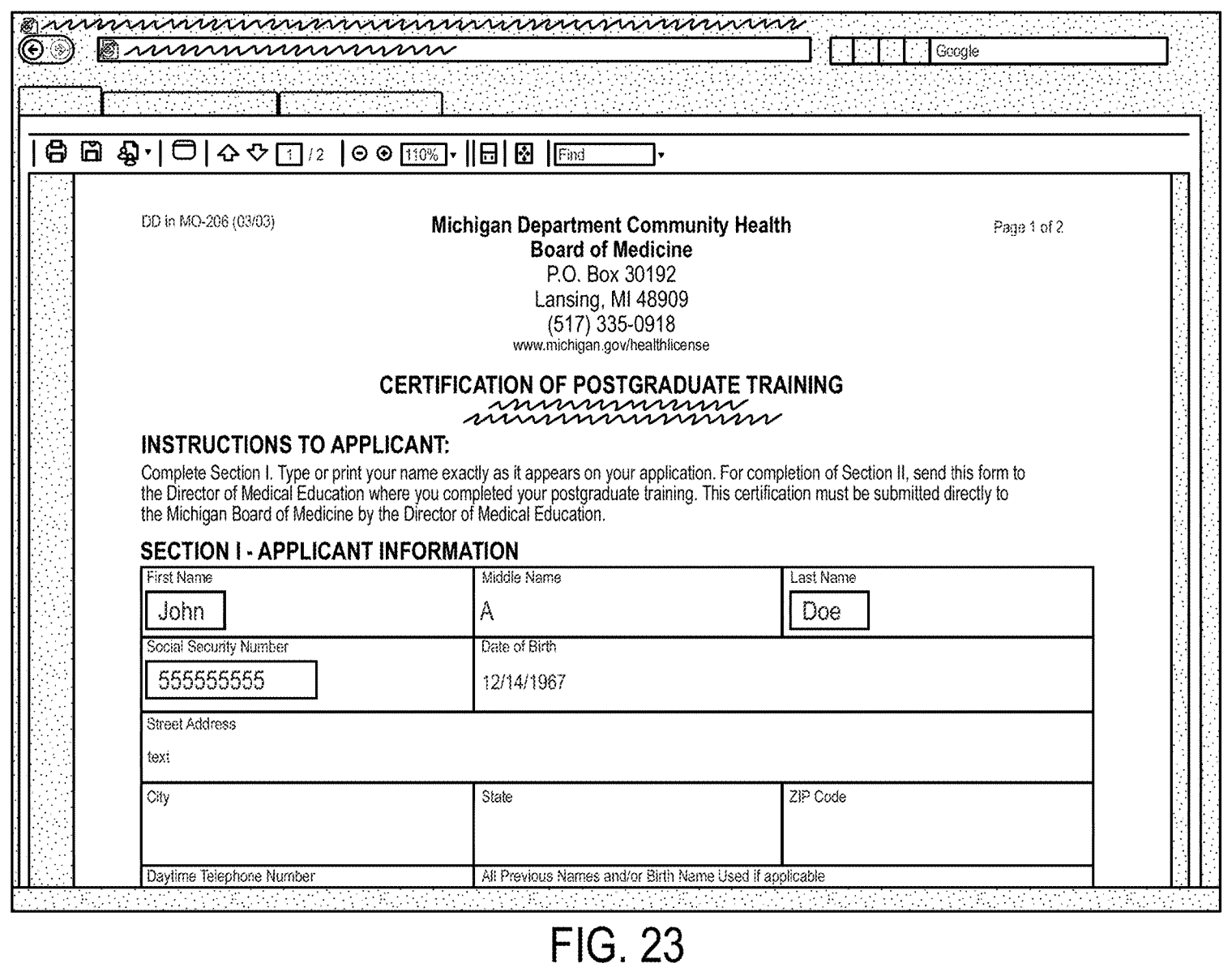

A preview or generate PDF button 1380 (FIG. 18) provided by the GUI allows a user to preview the form derived from the mapped schema. In this regard, selection of the generate PDF button 1380 causes retrieval of sample data from the object model, and then a display of the transformed data in the mapped form with the data automatically filled in based on the selected mapping. In this manner, the mapping user may verify that the mapping is correct. FIG. 23 is a screen shot of the form depicted in FIG. 19, with exemplary data filled in according to the mapping schema in the mapping table 1393 of FIG. 22. If any of the fields was mapped incorrectly, the mapping user may change the mapping information in the mapping table 1393 by selecting the edit button 1398 for the erroneously mapped field.

Upon verification that the mapping is correct, the mapping user selects a save to file button 1411 (FIG. 18) to store the mapping table 1393 into a designated map file (also referred to as association file). According to one embodiment of the invention, the map file is stored in the data storage device 1108 along with its metadata. Such metadata may include, for example, a form ID identifying the form that was mapped, a version of the form, healthcare entity providing the form, information on the person generating the map file, a date on which the map file was generated, status of the map file as being approved or pending, and the like. According to one embodiment of the invention, the map file is an XML file, although other types of encoding files conventional in the art may be used in lieu of an XML file.

In other embodiments of the invention, a publish button (not shown) may also be provided to move the generated map file to a staging area of the data storage device 1108. According to this embodiment, all map files in the staging area require approval by a reviewer/administrator. The server 1100 may provide a management portal that a mapping reviewer/administrator can access via the user device 1112 to review and approve all map files in the staging area. Once the map file is marked as being approved upon indication of approval by the reviewer/administrator, the map file may be transferred from the staging to a mapping database of the data storage device 1108.

Embodiments of the present invention are also configured to efficiently handle updates to forms as new versions of forms are introduced to replace older versions. According to one embodiment of the invention, the mapping engine may compare the fields of the old form with the fields of the new form, and upon a discrepancy in the fields, highlight the fields that are different in the new form. In many cases, the changes will be minor. Thus, instead of having a user re-create the entire mapping schema for a new version of the form, the mapping engine provides the option to copy a previous mapped schema for reusing any of the mapping data that remains intact. Unlike prior art methodologies where any updates to forms requires new programming to manually code each field to a corresponding database field, embodiments of the present invention allow the reusing of previous mapping schema for improved efficiency of the mapping process.

A person of skill in the art should appreciate that the visual mapping provided via the embodiments of the present invention allow the mapping to be carried out in a user-friendly, intuitive manner, that does not require low level manipulation of database fields or other programming knowledge. As a result, the mapping tool provided by embodiments of the present invention is more scalable for dealing with the vast amount of different forms in the healthcare industry. In addition, embodiments of the present invention handle changes to forms in a manner that maximizes the reusing of prior mapping data, again making the mapping tool highly efficient and scalable in handling those changes.

Figure 15:
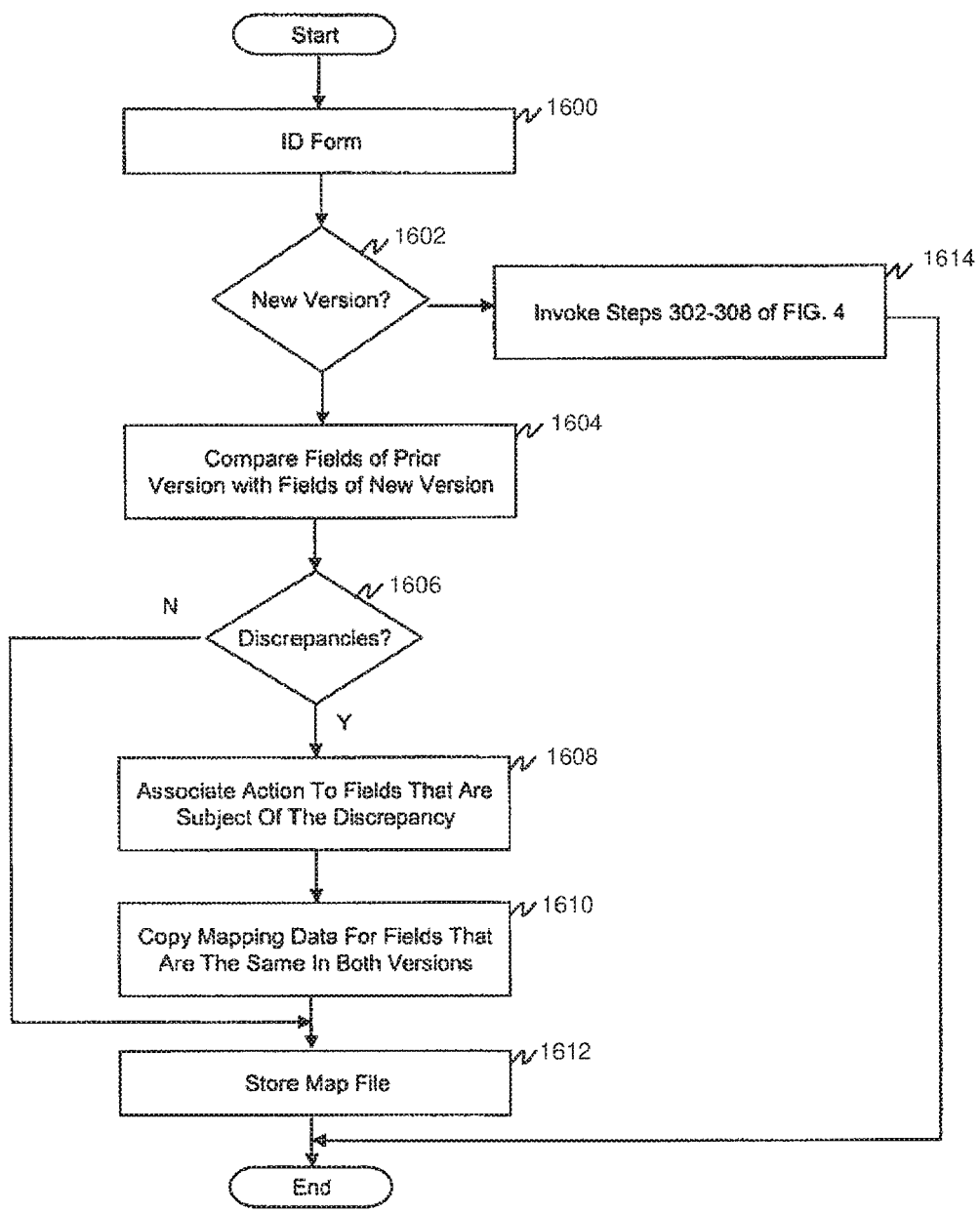
FIG. 15 is a flow diagram of a process executed by a mapping engine to generate a map file for a new version of a form that may contain updates, according to one embodiment of the invention.

FIG. 15 is a flow diagram of a process executed by the mapping engine 100a to generate a map file for a new version of a form that may contain updates, according to one embodiment of the invention. The process may be described in terms of a software routine executed by the processor in the server 1100 based on instructions stored in the server's memory. A person of skill in the art should recognize, however, that the routine may be executed via hardware, firmware (e.g., via an ASIC), or in any combination of software, firmware, and/or hardware. Furthermore, the sequence of steps of the process is not fixed, but can be altered into any desired sequence as recognized by a person of skill in the art.

In step 1600, the mapping engine 1100a identifies a form that requires mapping. In this regard, a user may select the form that is not marked as being mapped from the form library, and transmit his selection to the mapping engine. In another embodiment, the mapping engine 1100a may periodically check the status of the forms in the form library, and automatically identify those forms that require mapping. The mapping engine 1100a may then prompt a user to initiate mapping of those forms. In yet another embodiment, the prompt to the user to initiate mapping of the new form may occur as soon as the form is uploaded into the form library.

Once a determination is made that a mapping should be conducted, and the form that is the subject of such mapping has been identified, the mapping engine 1100a determines in step 1602 whether the identified form is a new version of a pre-existing form. If the answer is NO, steps 1302-1308 of the process depicted in FIG. 14 are invoked in step 1614.

If the answer is YES, and the form is a new version of a pre-existing form that has an older mapped version, the mapping engine 1100a proceeds to compare the fields of the prior version with the fields of the new version. In this regard, the mapping engine 1100a retrieves the encoding file (e.g., an XML file) for the prior version and the encoding file of the new version, and performs a compare operation for identifying discrepancies in the two files. Such a discrepancy may indicate a field ID and field name in the old version which is no longer found in the new version, or vice versa.

A determination is thus made in step 1606 as to whether discrepancies were found during the compare operation. If the answer is YES, the mapping engine 1100a associates one or more actions to fields that are the subject of the discrepancy. For example, if a field was added to the new version of the form, the field might be displayed in a highlighted form to notify the mapping user that the field needs to be manually mapped. Default text may also be added to the highlighted field. In response, the mapping user may, via a draft-and-drop process discussed above with respect to FIG.

14, map the added field to a corresponding object in the object model, and store the generated mapping data in a new map file.

If however, a field that used to exist in the old version of the fox in is no longer present in the new version, the mapping engine may simply display a notification to this effect for the mapping user.

In step 1610, the mapping engine 1100*a* proceeds to copy the mapping data for the fields that are the same in both versions of the form. In this regard, the mapping engine retrieves the map file for the prior version of the form using the reference information for the prior version of the form, and copies the mapping data for the fields that have not changed from the old version to the new version. The copied mapping data is then stored in step 1612 into the new map file.

Once a form has been mapped to a common object model, the fields of the form may be automatically populated/completed based on information stored with reference to the common object model.

Figure 16:
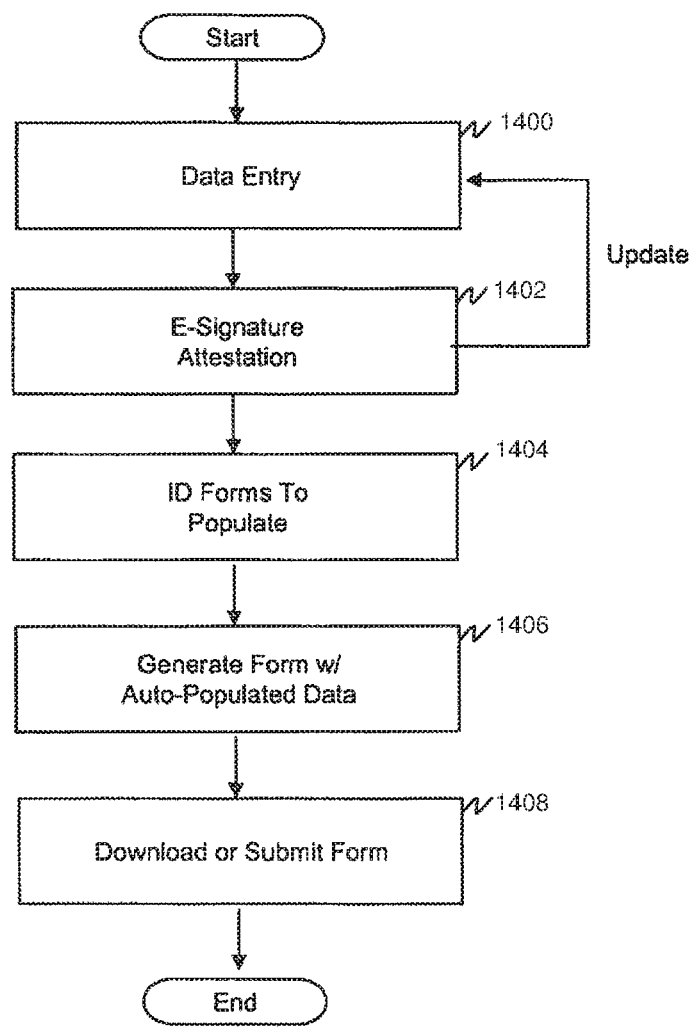
FIG. 16 is a flow diagram of an overall process for populating the object model with information of a particular provider and automatically generating a form with the fields pre-populated with the provided information according to one embodiment of the invention.

FIG. 16 is a flow diagram of an overall process for populating the object model with information of a particular provider and automatically generating a form with the fields pre-populated with the provided information according to one embodiment of the invention. The process may be described in terms of a software routine executed by the processor in the server 1100 based on instructions stored in the server's memory. A person of skill in the art should recognize, however, that the routine may be executed via hardware, firmware (e.g., via an ASIC), or in any combination of software, firmware, and/or hardware. Furthermore, the sequence of steps of the process is not fixed, but can be altered into any desired sequence as recognized by a person of skill in the art.

In step 1400, a provider or any other user of the system accesses a provider portal, such as, for example, one of the web portals 1100*b* hosted by the server 1100, to further access an application in the portal that captures data for populating the common object model 120. According to one embodiment of the invention, the application provides a universal online form generated based on the common object model that prompts the provider for information for populating the common object model. In this case, the provider himself is the source of the data, and may provide such data via any input device coupled to the provider device 1102. According to one embodiment of the invention, the universal online form is a web page or a set of web pages prompting a user to enter specific information pertaining to the user.

In other embodiments, the data is provided by one or more information sources 1106 such as, for example, schools, hospitals, insurance carriers, government agencies, and the like. The information sources may provide the data in electronic form (e.g., CD-ROM, email, scan, fax, etc.), via paper-based forms, or directly enter the data online via the web portal 1100*b*. The data may also be gathered automatically from the information sources 106 via use of web crawlers and the like. In yet another embodiment, a form that has been mapped to the common object model may be source of the data for populating the common object model. That is, instead or in addition to filling out the universal form, a user may also directly fill out a specific type of form for which mapping data exists. The form may be filled out online via the web portal 1100*b*, or offline first, and a copy of the completed form provided to the server in electronic form (e.g., CD-ROM, email, scan, fax, etc.). All or portions of the common object model may then be populated based on the information provided in the specific form.

In step 1402, the user provides his or her e-signature for being stored in the data storage device 1108, along with the provider's attestation that the information being provided is accurate and current. The information provided to populate the common object model may also be verified as described in the above-referenced U.S. Pat. No. 7,529,682. The provider may also periodically update the information as needed, with or without the benefit of alarms or prompts by the server.

According to one embodiment of the invention, the server 1100 may be configured to take all or a portion of the data used to populate the common object model and search a plurality of different information sources 106 to verify that the information is accurate. For example, the server 1100 may be configured to compare information stored at the information sources with the information provided by the provider for determining whether there are any inconsistencies. Such information sources 1106 may be social networking sites, information databases, or any other body of information conventional in the art. Any mechanism for identifying, accessing, and comparing the information may be utilized as will be apparent to a person of skill in the art. The server 1100 may be configured to transmit an alarm to the provider, healthcare entities, information sources, governmental agency, or any other entity identified by the server, upon a discrepancy in the information being compared.

According to one embodiment of the invention, the provider may need a form generated and submitted to a healthcare entity. For example, the provider may need to submit an enrollment form to enroll in a particular health plan, and may access the provider portal to request such form. Other healthcare entities may also trigger the generating of forms. In either scenario, the provider portal invokes the runtime engine 1100*c* and identifies, in step 1404, a particular form to populate and generate.

In step 1406, the runtime engine generates the form with automatically populated data obtained from the provider object model. In this regard, the runtime engine may assume that the form is to be automatically populated with the data stored in the common object model upon the user selection of the form, which then eliminates the need for manual filling out of the fields by the user. Alternatively, the user may be given the option to manually enter all or some of the data if the user does not want the form automatically populated.

In step 1408, the runtime engine receives a request to download the form to the provider device, or to automatically submit the form to a recipient that interfaces with the server, such as, for example, a healthcare entity device 1104. According to one embodiment of the invention, the interface is an application program interface (API) that allows all form data to be submitted directly to the recipient via an API channel according to conventional mechanisms.

Figure 17:
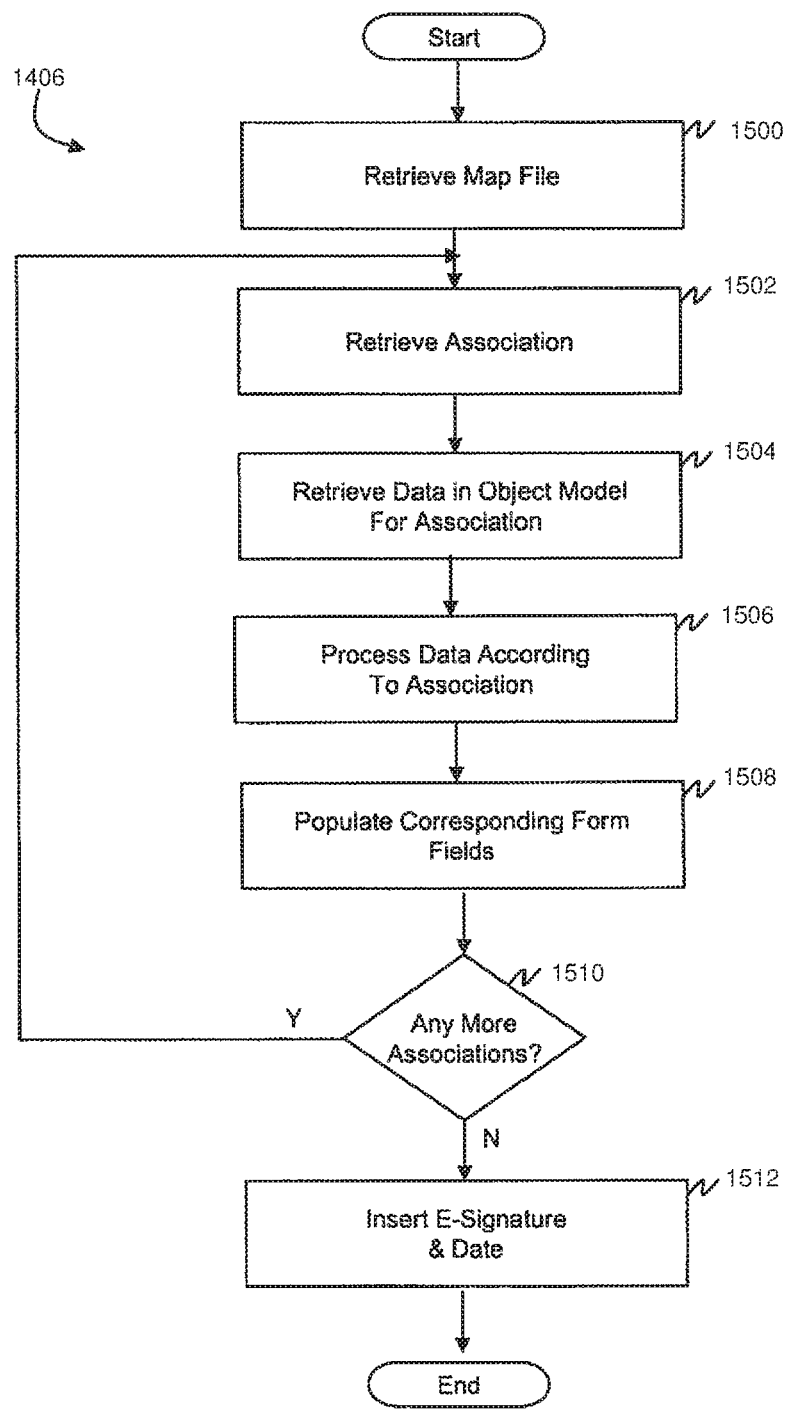
FIG. 17 is a more detailed diagram of a step for generating a form with automatically populated data according to one embodiment of the invention.

FIG. 17 is a more detailed diagram of step 1406 of generating a form with automatically populated data according to one embodiment of the invention.

In step 1500, the runtime engine uses the form ID corresponding to the selected form, and retrieves a corresponding map file from the mass storage device 1108.

In step 1502, the runtime engine retrieves a stored association from the map file. In this regard, the association identifies the one or more object attributes or properties mapped to a particular field of the form, along with any transformation or aggregation functions that are to be performed for the association.

In step 1504, the runtime engine uses an instantiation of a data access layer and uses the layer components to retrieve data stored for the identified object attribute or property.

In step 1506, the runtime engine processes the retrieved data according to the retrieved association. In this regard, the runtime engine identifies any conversion and/or aggregation rule indicated for the association, and invokes the appropriate algorithm(s) for processing the retrieved data according to the conversion and/or aggregation rule. The processing may be as simple as making a copy of the retrieved data for entering the data as-is into the corresponding form, such as, for example, if the aggregation is a direct mapping of the data. For other types of conversions and/or aggregations, the algorithm may require transformation, derivation, and/or concatenating of the data, as well as inserting spaces or text (e.g., hyphens, commas, semi-colons, etc.).

In step 1508, the runtime engine uses the processed data to automatically populate the corresponding form field.

In step 1510, a determination is made as to whether there are any other associations in the map file that need to be processed for auto-populating the form. If the answer is YES, the runtime engine returns to step 1502 to process the other associations. Otherwise, if the answer is NO, the runtime engine pulls, in step 1512, a stored e-signature of the provider for whom the form is generated, as well as a date, and enters this information into corresponding fields of the form. The form is then ready to be displayed on the provider device 1102 for review by the provider. The provider may review and make any needed updates to the pre-populated information, and/or manually enter information for any fields that have not been automatically pre-populated. The form is then ready to be downloaded to the provider, or to be submitted directly to a healthcare entity coupled to the server. In this regard, the web portal 1100b may provide a "download" option which causes transmitting a copy of the filled form for storing in a data store coupled to the provider device. The web portal 1100b may also provide a "submit" option which prompts the user to enter information of the entity (e.g., an email address) who is to receive a copy of the filled form.

Although this invention has been described in certain specific embodiments, those skilled in the art will have no difficulty devising variations to the described embodiment which in no way depart from the scope and spirit of the present invention. Furthermore, to those skilled in the various arts, the invention itself herein will suggest solutions to other tasks and adaptations for other applications. For example, although may of the forms used in the exemplary embodiments relate to healthcare forms, a person of skill in the art should recognize that embodiments of the present invention applies to other fillable forms used in other fields. It is the Applicant's intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

Peer Referencing

During the process of applying to practice in or be affiliated with an institution, such as, for example, a healthcare institution, practitioners are often asked to provide qualified peer references as part of the application. In the healthcare field, a peer generally refers to a healthcare professional practicing in the same area of specialization as the provider.

Peer references are also often required when a healthcare organization appoints an individual to the medical staff or grants initial clinical privileges to the individual. The process of identifying peers that meet all regulatory and compliance standards as well as reaching out to these peers to verify detailed information is very cumbersome and time consuming. Strict processes and regulations also generally need to be met for the selection of peers that are qualified to provide healthcare peer references that may be accepted as valid. Prior art systems do not provide a mechanism for one provider to take advantage of loosely constructed social networks to automate the peer referencing process in a manner that satisfies those strict processes and regulations. However, if an individual can register with an online system, for example, by providing professional and personal data, and/or other selected criteria common to a significant numbers of the users, the user can be linked to a plurality of other such individuals who may be qualified to provide online peer references.

In general terms, embodiments of the present invention are directed to a system and method for connecting healthcare providers via an online portal to allow the providers to generate a network of peers for facilitating the providing and obtaining of peer references. The online portal provides a user interface, such as, for example, a graphical user interface (GUI), that displays and allows searching of peers who are qualified to provide peer references, and facilitates interaction among such peers. The user interface also facilitates the obtaining of training, work history, specialty and other credentials data for use in determining, for example, qualification of the users for providing peer reference to other users.

A rules engine applies rules and logic to aggregated credentials and relationship data of the registered providers to identify users of the system who are qualified to provide a peer referral for a particular provider. A peer in a provider's network may provide a peer reference needed by the provider to access certain medical privileges. The peer reference data may be provided as answers to a structured questionnaire. The answers may then be used to automatically populate a specific peer referral form.

According to one embodiment, the system includes a database for storing the credentials and relationship data of the healthcare providers of the system. According to one embodiment, the rules engine aggregates and maps the data to create a virtual professional relationship network with clear structure of qualified versus unqualified peers. For example, a qualified peer for a particular provider may be defined as someone who knew the provider in the last three to five years in a professional setting, and such a relationship may be depicted in the provider's relationship network.

According to one embodiment, users may invite peers to join the system and become a peer to the inviting user. Invitations may be sent, for example, by e-mail, fax, or any other electronic communications medium conventional in the art. The invited peer may accept the invitation, in which case he or she becomes a user of the system as a peer of the inviting user. The new user is then prompted to provide credential data, relationship data, and other types of data for determining his or her qualifications for providing a peer reference.

According to one embodiment of the invention, peers in the system further have the ability to provide information about one another regarding professional qualifications, competencies, and the like. In order for a peer to provide a reference for another provider, for example, the pre-qualified peer might fill-in a structured questionnaire about the provider's clinical competency and the like.

Figure 24:
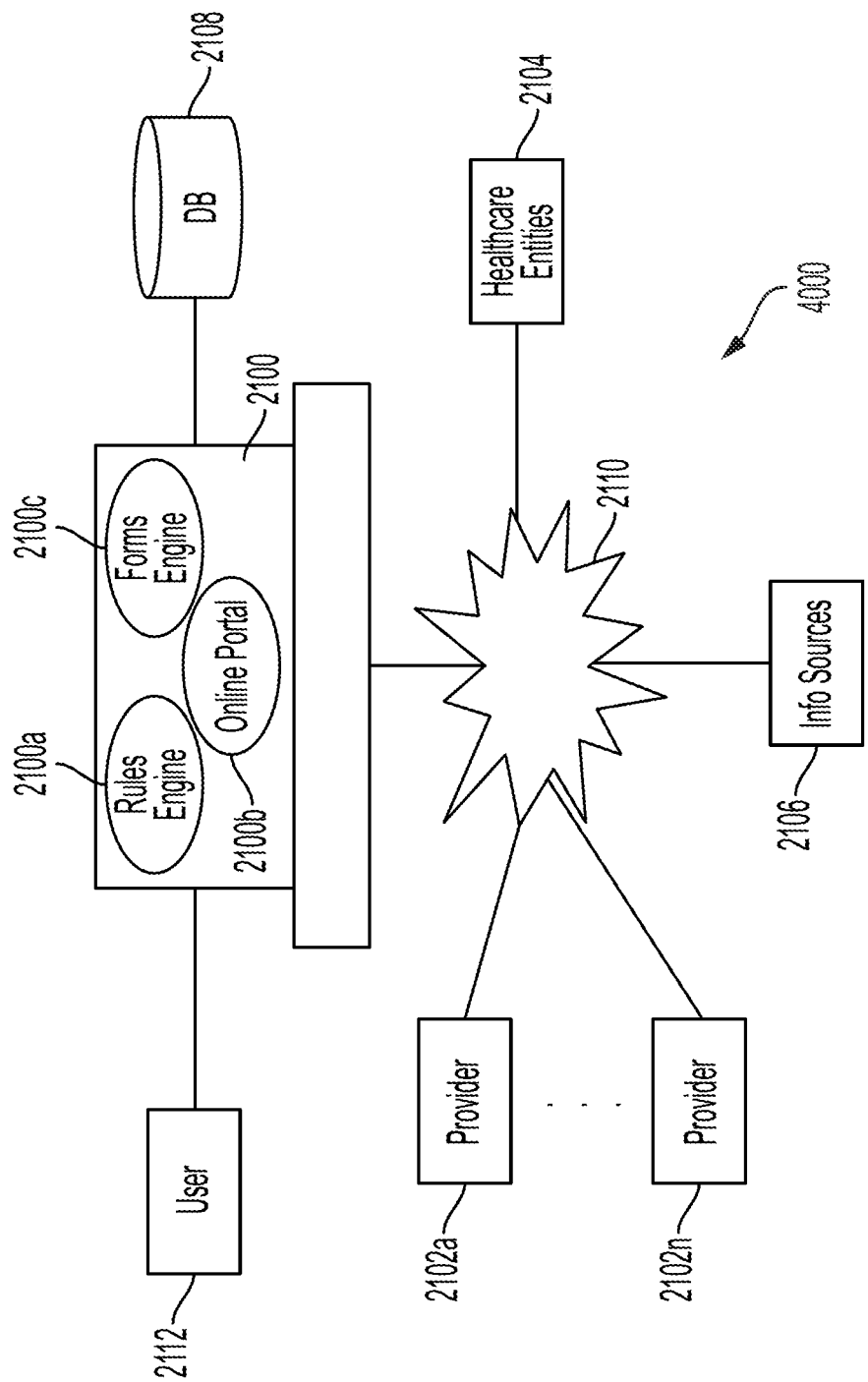
FIG. 24 is a schematic block diagram of a system for peer referencing according to one embodiment of the invention.

FIG. 24 is a schematic block diagram of a system 4000 for peer referencing according to one embodiment of the invention. The system 4000 includes one or more remote healthcare provider devices 2102a-2102n, healthcare entity devices 2104, and information sources 2106 (collectively referred to as remote devices), coupled to one or more servers 2100 over a data communications network 2110. The communication network 2110 may be a network or combination of networks spanning any geographical area, such as a local area network, wide area network, regional network, national network, and/or global network. The Internet is an example of a current global computer network. In addition, the communication network may be a hardwire network, wireless network, or a combination of hardwire and wireless networks.

Hardwire networks may include, for example, fiber optic lines, cable lines, ISDN lines, copper lines, and the like. Wireless networks may include, for example, cellular systems, personal communications service (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

Each of the remote devices may be any processor controlled device that permits access to the communication network 2110, including terminal devices, such as personal computers, workstations, servers, clients, mini-computers, main-frame computers, laptop computers, a network of individual computers, mobile computers, palm-top computers, hand-held computers, set top boxes for a television, other types of web enabled televisions, interactive kiosks, personal digital assistants, interactive or web enabled wireless communications devices, mobile web browsers, or a combination thereof.

In this regard, the remote devices include a processor, memory, and one or more input devices such as a keyboard, mouse, touch pad, joystick, pen input pad, and the like. The remote devices may also include an output device, such as a display screen and audio output. The memory included in each remote device stores computer program instructions which, when executed by the processor, causes the processor to perform certain actions mandated by the computer program instructions. Such computer program instructions may also be stored in a disk, CD, flash drive, or other non-transient computer readable media.

The server 2100 is a data processing apparatus with one or more processors and memory storing computer program instructions for adapting the computer to generate a network of peers for obtaining peer references. The server 2100 may be similar to the server described in the above-referenced U.S. Pat. No. 7,529,682. The server 2100 may be hosted by a particular healthcare entity such as, for example, an insurance company, hospital, surgical center, or the like. According to one embodiment, the server may be configured to provide the electronic credentials verification and management functionalities described in U.S. Pat. No. 7,529,682. The server 2100 may also be configured to map various healthcare administrative forms, referral forms, and the like, to a common object model, and automatically populate those forms based on data provided by a qualified peer, healthcare provider, or other information source, as is described in the above-referenced U.S. Pat. No. 8,850,304, which issued from application Ser. No. 13/022,550.

According to one embodiment of the invention, the server 2100 is accessed by users who register with the server and who can then connect with other users to form a network of peers. The server is configured to automatically determine whether a peer in the user's network, or another user who has not yet been identified as a peer for a particular user, is qualified to provide a peer reference for the user. The server may then be configured to transmit a request to provide a peer reference for the particular user upon command by the user.

In this regard, the server 2100 includes a rules engine 2100a, online portal 2100b, and a forms engine 2100c. According to one embodiment, the online portal 2100b provides a graphical user interface for registering with the server, building a peer network, submitting forms to various healthcare entities, requesting peer references from qualified peers, and the like. The rules engine 2100a is configured to apply rules and logic to aggregated credentials and relationship data of the registered healthcare providers to create a virtual professional relationship network for each provider. The forms engine 2100c generates forms with fields automatically populated based on data associated with a particular provider for submitting to the provider, different healthcare entities, and the like. For example, the forms engine 2100c may be invoked to automatically populate a peer referral form for an individual based on information provided by a peer referral source for then submitting to a requesting healthcare entity. According to one embodiment, the forms engine may include a mapping engine for mapping fields of different referral forms to a common object model, and a runtime engine for automatically populating fields of the referral forms based on data stored in the common object model. The mapping and runtime engines are discussed in further detail in the above-referenced U.S. Pat. No. 8,850, 304.

The engines 2100a, 2110c and portal 2100b may be implemented as software modules that are executed by a processor in the server based on computer program instructions stored in memory. Each of the engines and portal may implemented as a separate software module, or one or more of the engines or portal may be combined into a single module or further divided into one more sub-modules as may be appreciated by a person of skill in the art. A person of skill in the art should recognize that the modules may also be implemented in hardware, firmware (e.g., ASIC), or a combination of hardware, firmware, and/or software.

According to one embodiment of the invention, a user device 2112 may be coupled to the server 2100 via a communications link 2114. The user device 2112 may be similar to any of the remote devices described above. The communications link 2114 may be a direct wire, an infrared data port, a wireless communications link, global communications link such as the Internet, or any other communications medium known in the art. The user device 2112 allows an administrator to access the server 2100 for performing management functions such as, for example, updating rules accessed by the rules engine 2100a, updating forms accessed by the forms engine 2100c, and/or performing other administrative and maintenance tasks.

The data storage device 2108 may be any hard disk drive or drive array which hosts a number of purpose-built databases and files useful for implementation of the system 4000. For example, the data storage device may take the form of a hard disk or disk array, storing a provider's profile, work history, credentialing information, networking database with information on the provider's peer network, healthcare forms, peer referral forms and questionnaires, healthcare and information of other entities associated with the system. Any electronic healthcare form may be mapped and stored in the data storage device.

According to one embodiment, the data storage device 2108 hosts a networking database with relationship information for the registered users of the system. In this regard, each provider provides his or her professional background and credentialing information via the online portal 2100*b*, and the information is used to construct a comprehensive database of providers as well as update the networking database with relationship information. The information and defined relationships in the networking database can then be utilized by users and systems to guide the selection of peers and the acceptance of qualified references.

According to one embodiment of the invention, each provider accesses the online portal 2100*b* to register with the server 2100. In this regard, the provider is prompted to provide information on his professional background, work history, credentials, and the like, all of which is then stored in one or more databases of the data storage device 2108, such as for example, a credentials database and/or networking database. According to one embodiment of the invention, the information is provided by the user by filling out a universal online form provided by the online portal 2100*b*. The information is then used to populate a common object model as described in the above-referenced U.S. Pat. No. 8,850,304. The provider may also access the online portal 2100*b* to create and maintain his profile and credentialing data for verification, forms generation, and the like. The server may query one or more information sources 2106 to verify the information provided by the user, as is further described in the above-referenced U.S. Pat. No. 7,529,682.

Once registered with the server 2100, but before or after having provided all of the provider's background or credentials information, each provider may access the online portal 2100*b* to build his or her peer network of providers. According to one embodiment, the peer network includes a list of users who are enrolled/registered with the server 2100, whom have been deemed to be qualified to provide peer references for the provider, and with whom connections have been formed for viewing and exchanging information that may not be available to users who are outside of the provider's peer network.

In building a peer network, the provider accesses the networking database via the online portal 2100*b* to find, invite and connect to other providers. For example, the provider may search for other providers enrolled/registered with the server 2100, and view the public profiles of such providers for determining whether to add them to his or her network. Qualified peers may also be recommended to the provider based on information in the networking database. The online portal 2100*b* may include a messaging engine which may be invoked by the user to send invitations to other providers to join his/her network.

According to one embodiment of the invention, a peer in a provider's network may provide a peer reference needed by the provider to access certain medical privileges or to qualify to perform certain medical procedures. Due to the rigorous criteria that need to be met in order for a peer reference to be acceptable, it is desirable to identify those peers in the network that meet those standards prior to requesting a peer reference from them. For example, a peer may be deemed to be qualified to provide a peer reference to a provider for a particular privilege if the peer is in the same specialty as the provider, has worked in the same facility, shares the same privilege, and can comment on the skills of the practitioner. Additional or other criteria may also be considered by the rules engine 100*a* in determining whether a peer in an individual's peer network is qualified for providing a peer referral.

In this regard, the rules engine 2100*a* accesses the network database to access information on peers in the individual's peer network. According to one embodiment of the invention, the rules engine automatically processes the information of peers in the peer network against one or more rules for automatically identifying qualifying peers for peer referencing. The server then transmits requests for peer referencing to the identified peers over the data communications network. In response to the request, the identified peers may submit a peer reference in a paper-based or electronic format. According to one embodiment, the server may access the forms engine 2100*c* to retrieve and transmit dynamic peer reference questionnaires and/or forms that tailor to each type of provider and privilege being pursued. As networked users grow in size exponentially, identifying qualified peers and requesting them to go through structured peer referencing questionnaires to meet specific peer referencing standards may be substantially more straight forward than compared to existing processes.

According to one embodiment of the invention, the peer providing the reference or the provider requesting the reference may access the online portal 2100*b* and select an online reference form to be automatically populate based on responses to questionnaire questions by the peer reference. The generating and populating of the fields of the form may be carried out as is discussed in the above-referenced U.S. Pat. No. 8,850,304. The auto-populated form may then be downloaded to the peer, the provider, and/or submitted directly to a healthcare entity requesting the peer reference.

According to one embodiment of the invention, the rules engine 2100*a* may also be invoked to identify users who are enrolled in the system who would qualify to provide a peer reference to a particular individual, but who are not yet part of the individual's peer network. Once identified, the rules engine 2100*a* may suggest that the individual be added to the individual's peer network. The individual may act upon the suggestion and send an invitation to the identified users to join his or her peer network, before requesting a peer referral from those users.

Figure 25:
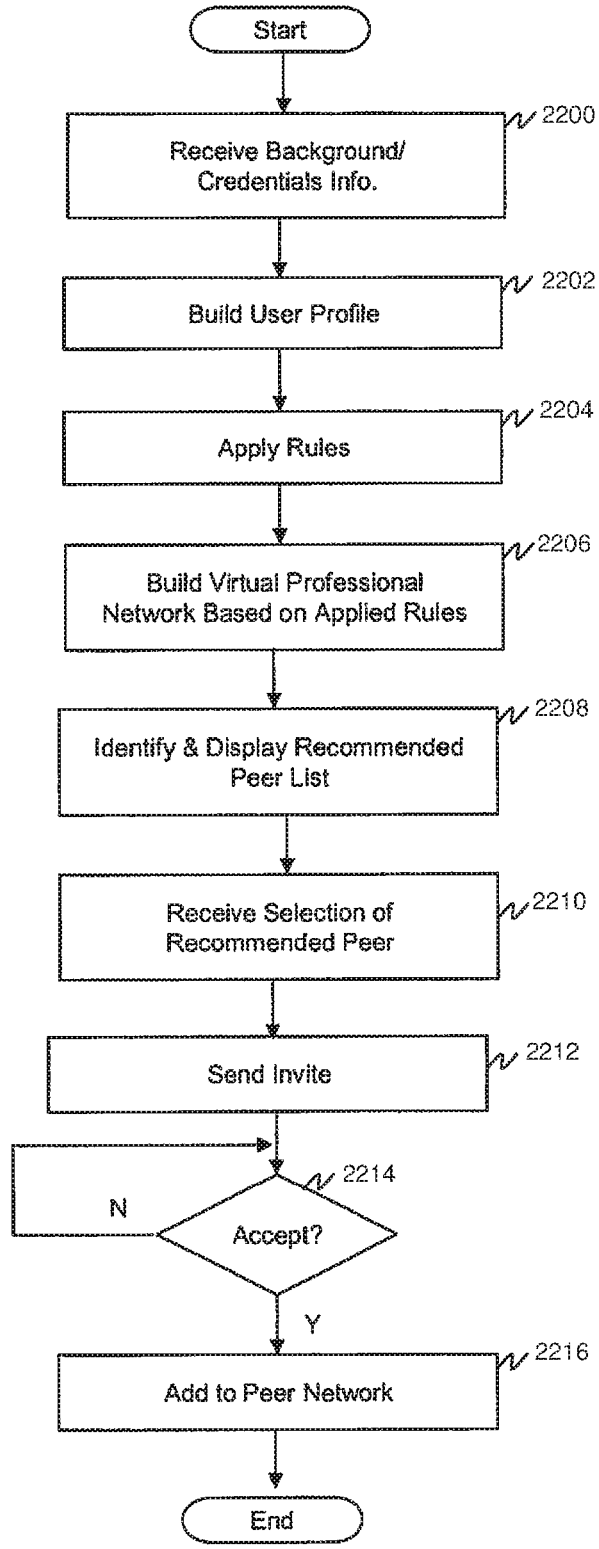
FIG. 25 is a process flow diagram of a process for building a peer network for a particular user according to one embodiment of the invention.

FIG. 25 is a process flow diagram of a process for building a peer network for a particular user according to one embodiment of the invention. The process may be described in terms of a software routine executed by the processor in the server 2100 based on instructions stored in the server's memory. The instructions may also be stored in other non-transient computer readable media such as, for example, a disk, CD, flash drive, or the like. A person of skill in the art should also recognize that the routine may be executed via hardware, firmware (e.g., via an ASIC), or in any combination of software, firmware, and/or hardware. Furthermore, the sequence of steps of the process is not fixed, but can be altered into any desired sequence as recognized by a person of skill in the art.

The process starts, and in step 2200, the user accesses the online portal 100*b* to provide or update his information, such as, for example, his background and credentials information. In this regard, the user may navigate to an application page provided by the online portal and enter the information prompted by the page. If the information is to be updated, the user may retrieve his or her user record for display instead of the application page.

According to one embodiment of the invention, the online application is a universal application which is mapped to a common object model. As the user provides his or her information, the data may be used to populate the objects of the common object model.

In step 2202, the online portal 2100b builds or updates a user profile for the inputting user. In this regard, the online portal 2100b generates or updates a user record with credentials and relationship data for storing in a credentials database of the data storage device.

In step 2204, the rules engine 2100a is invoked for employing a set of rules and logic for constructing or updating the user's virtual professional network. In this regard, the rules engine 2100a may traverse a virtual peer identification decision tree to identify the relationship of the user with other users of the system, and determine whether a qualification criteria has been satisfied. As a result of traversing the decision tree, the rules engine 2100a identifies a user being evaluated as a qualified peer or not. According alternative embodiments, the rules engine 2100a may be configured to assign a score to each other user reflecting the extent of the qualifications of the peer to provide peer referencing.

In step 2206, the rules engine 2100a constructs the virtual professional network based upon evaluation of the various registered users of the system and their relationship to the particular user. The virtual professional network may be as simple as a list of the users of the system who have been identified as qualified peers, and an association of that list to the particular user. Such information may be maintained in the relationship database. The virtual professional network may also be depicted visually as a network graph showing connections between the particular user and all other users who are deemed to be qualified peers to the particular user. As a person of skill in the art will appreciate, the virtual professional network is dynamic and constantly evolving as other users enroll with the server and as information on the users are updated. The update of the virtual professional network may require execution of steps 2204 and 2206 from time to time (e.g., based on a pre-defined schedule or on a random basis), or in response to particular monitored events, such as, for example an update to a criteria being monitored in any user's profile, in response to a user command to display an updated list of qualified peers, a change of rules for determining qualifications of a peer, or the like. The update may include adding or deleting users to the virtual professional network. For example, a user deemed to be a qualified peer for providing a peer recommendation at one point in time may be deleted as such at some other point in time.

In step 2208, the online portal 2100b identifies a recommended peer list based on the user's virtual professional network, and displays the list via a graphical user interface. According to one embodiment, the display of the recommended peer list is pushed to the user without the user manually requesting the recommendations. The user may also make a manual request for qualified peers whenever a peer referral is needed.

In step 2210, the online portal 2100b receives a selection of a recommended peer, and in step 2212, transmits an invitation to the selected peer for joining the user's peer network. A determination is made in step 2214 as to whether the peer has accepted the invitation. If the answer is YES, the online portal adds the peer to the user's peer network in step 2216. In this regard, the user's profile may be updated to include information on the accepting peer as being a member of the user's peer network. Information on the user's peer network may also be maintained separately in the network database.

Figure 26:
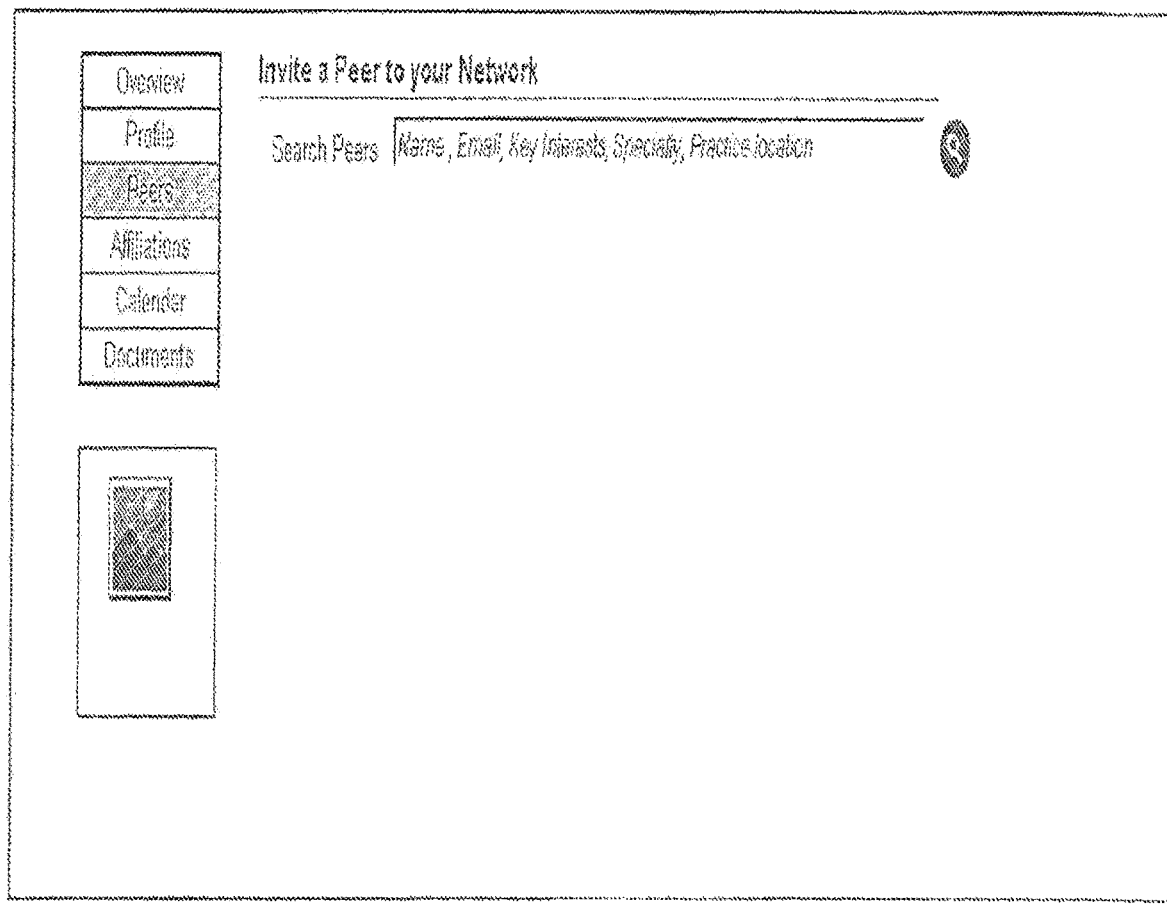
FIG. 26 is an exemplary screen shot of a screen for searching for peers to invite for joining a user's peer network according to one embodiment of the invention.

FIG. 26 is an exemplary screen shot of a screen for searching for peers to invite for joining a user's peer network according to one embodiment of the invention. A user may search for different types of users registered with the server. For example, the user may conduct a search based on name, email, interests, specialty, practice location, and the like. Upon entry of such a search request, the online portal 2100b conducts a search of the user's virtual professional network by accessing data stored in the relationship database, and retrieves a list of qualified peers matching the search criteria.

Figure 27:
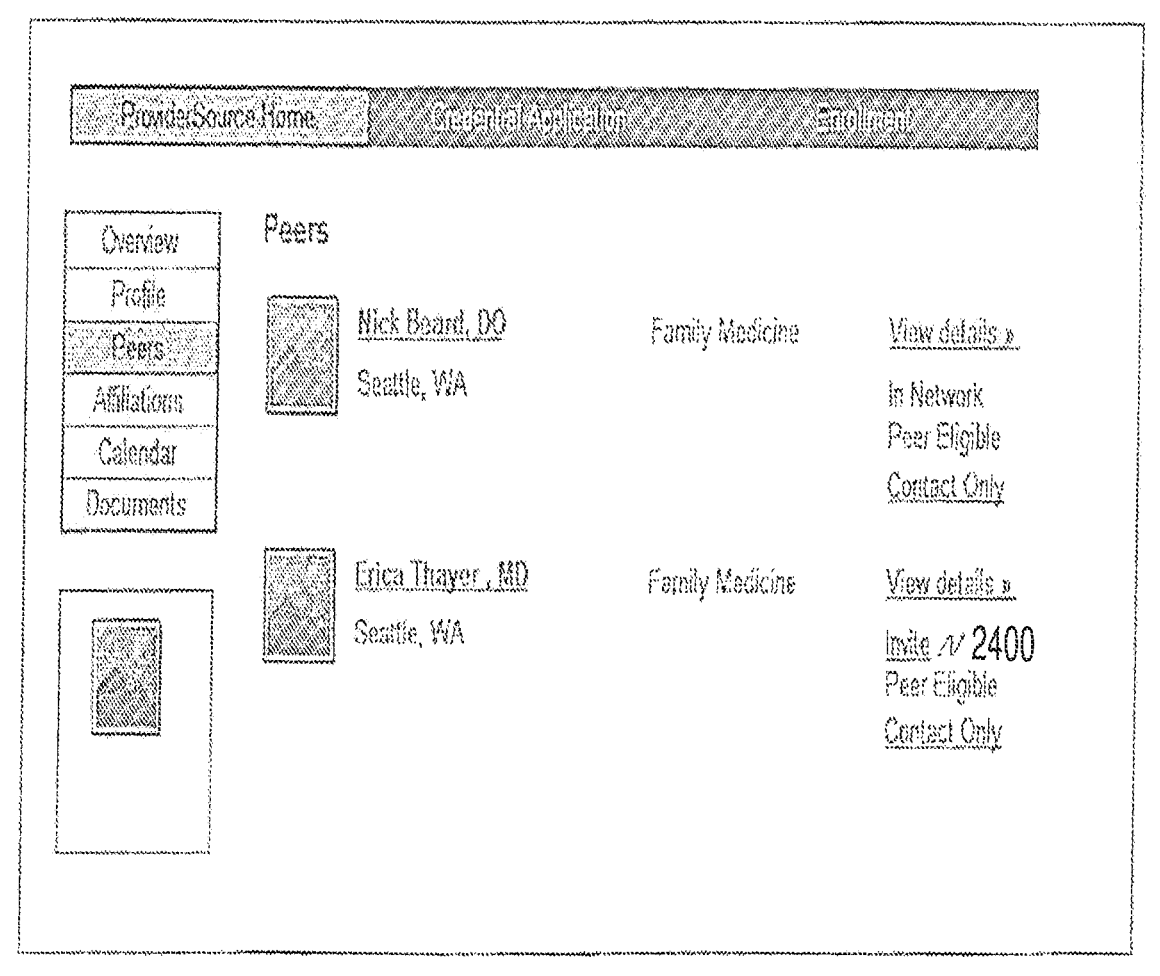

FIG. 27 is an exemplary screen shot of a screen listing peers that are available for inviting into a user's peer network according to one embodiment of the invention. According to one embodiment, the resulting peers are peers who are in the user's virtual professional network who are deemed to be qualified to provide a peer reference to the user. According to one embodiment, if a user is enrolled in the system but is not deemed to be a qualified peer, such information may be displayed to the user conducting the search. Alternatively, both qualifying and non-qualifying peers may be listed as potential peers for inviting to join a user's network. In either case, the user may send an invitation message to join his or her peer network upon selection of an invite option 2400.

Figure 28:
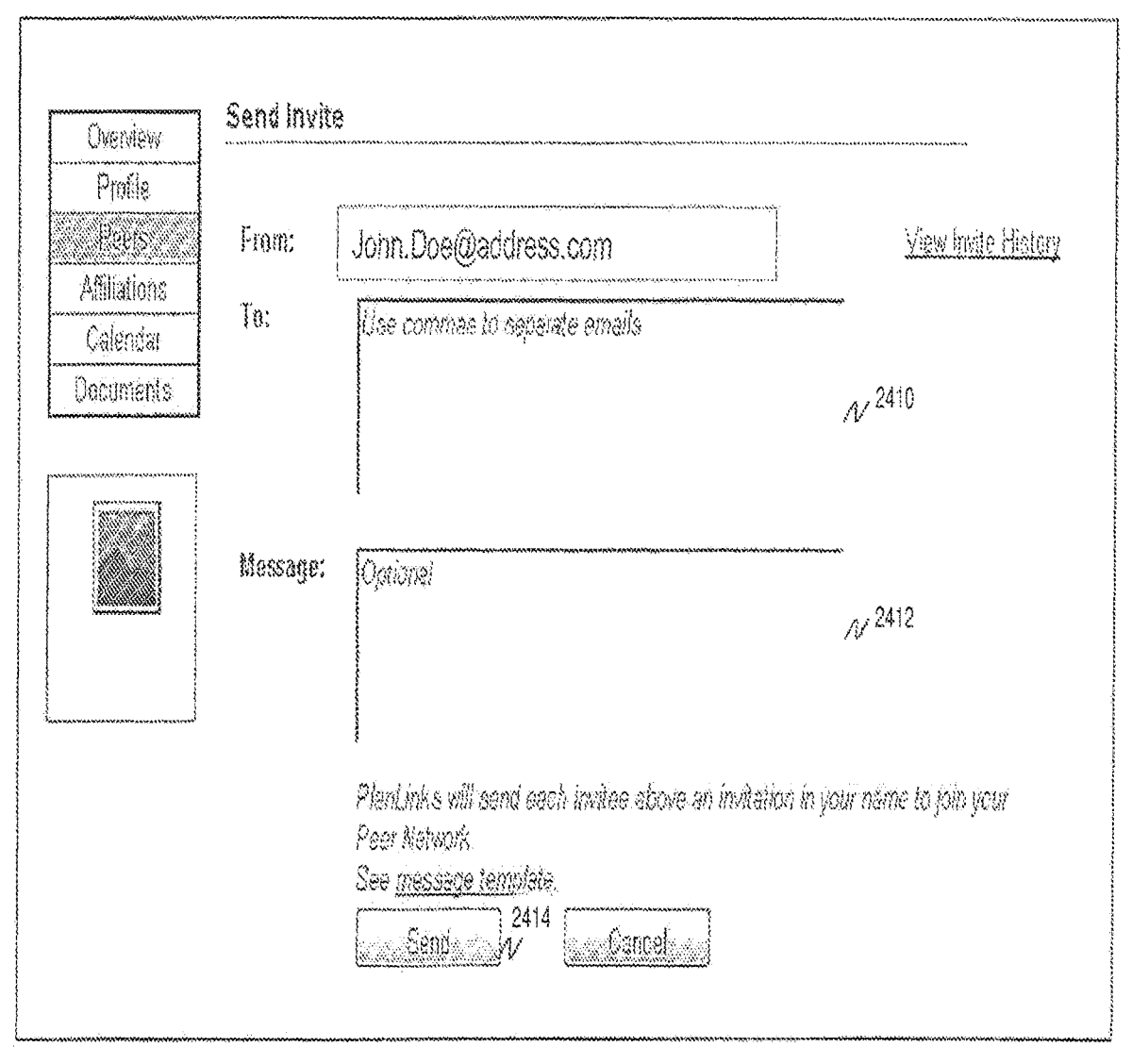

FIG. 28 is an exemplary screen shot of an invitation message for inviting peers to join a user's network according to one embodiment of the invention. The user manually enters into box 2410 emails of the peers he or she wants to invite, or such information may be automatically inserted by the server based on user selection of the invite option 2400 for a specific user. The inviting user may provide an optional message in box 2412, and transmit the invitation upon actuating a send button 2414.

Figure 29:
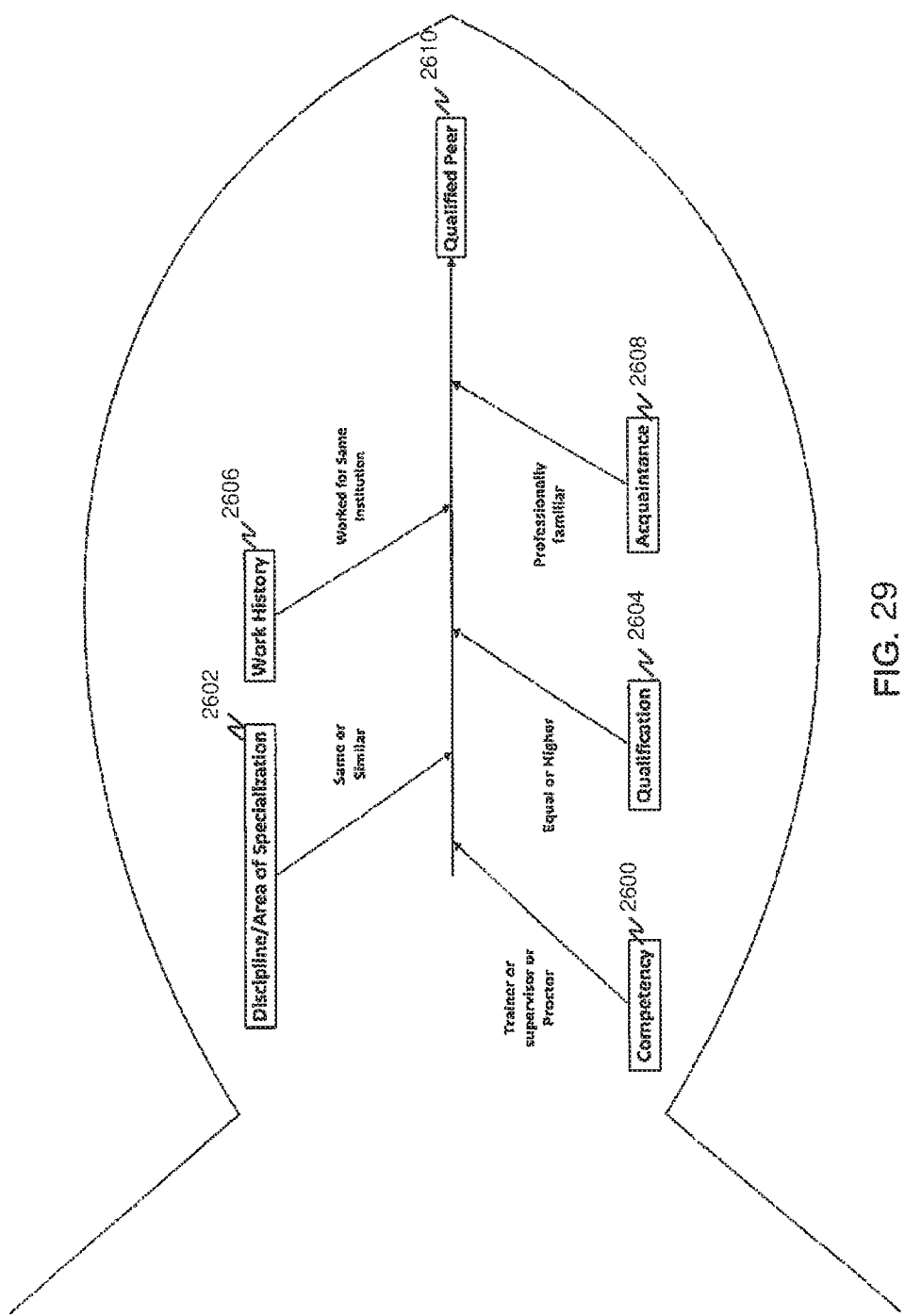
FIG. 29 is a schematic diagram of a virtual peer identification decision tree according to one embodiment of the invention.

FIG. 29 is a schematic diagram of a virtual peer identification decision tree according to one embodiment of the invention. The decision tree is invoked by the rules engine 2100a in step 2202 of FIG. 25 to construct a particular individual's virtual professional network. The decision tree is traversed by the rules engine for evaluating various factors/criteria of the tree that are used to determine whether the registered users of the system are qualified to provide a peer reference for the particular individual. The qualification criteria that may be evaluated include, but are not limited to, a competency criteria 2600, discipline/area of specialization criteria 2602, qualification criteria 2604, work history criteria 2606, acquaintance criteria 2608, and the like.

According to one embodiment, the rules engine retrieves from the data storage device a user record with the profile information for each user, and compares the data stored for the user for determining whether all (or in some embodiments, a portion) of the qualification criteria have been satisfied. For example, in evaluating the competency criteria 2600, the rules engine may determine based on profile data retrieved for the user and the individual, whether the user was a trainer, supervisor, or proctor for the individual. In order to make this evaluation, the user's profile may include a competency field, which may include information of different people whom the user has trained or supervised, a department or group for which the user was in charge, or the like. The competency leg of the evaluation may be deemed to have been satisfied if the user was a trainer or supervisor for the particular individual.

In considering the discipline/area of specialization criteria 2602, the rules engine 2100a may determine whether the user's discipline or area of specification is same or similar to the particular individual's discipline or area of specialization. In order to make a determination as to whether one discipline/area of specialization is similar to another, the rules engine may examine a table that includes, for each discipline/area of specialization, a list of other disciplines and areas of specializations that are deemed to be similar. If the discipline or area of specification is deemed to be the same or similar, the discipline/area of specification criteria may be deemed to have been satisfied.

In considering the qualification criteria 2604, the rules engine may determine whether the user's qualifications they are equal or higher to the particular individual's qualifications in order to determine that the qualification criteria has been satisfied. The user's work history 2606 may also be evaluated to determine whether the user worked in the same institution as the individual. If so, the work history criteria may be deemed to have been satisfied. In addition, the acquaintance criteria 2608 may be evaluated for determining whether the user and individual are familiar to each another in the professional field. For example, if the user and individual have appeared together in a same professional conference, were co-authors of a publication, or are listed as being members to a same organization or charter, the acquaintance criteria may be deemed to be satisfied for the particular user being evaluated. In this regard, the rules engine 2100a may compare the papers, organizations, charters, and the like, listed by the user and the individual, for any overlaps.

The satisfying of each qualification criteria of the decision tree causes the rules engine 2100a to proceed to an analysis of a next qualification criteria. Otherwise, the rules engine 2100a stops the evaluation process and concludes that the user is not a qualified peer referral source. Affirmative answers to all the criteria being evaluated causes a conclusion that the user is a qualified peer 2610. Alternatively, scores may be assigned to each leg of the evaluation and a determination of whether a user is a qualified peer or not may depend on whether an overall score assigned to the user satisfies a minimum threshold score. The score may also be weighted based on how important the particular data being analyzed is in order to judge the user's competency as a peer reference.

Figure 30:
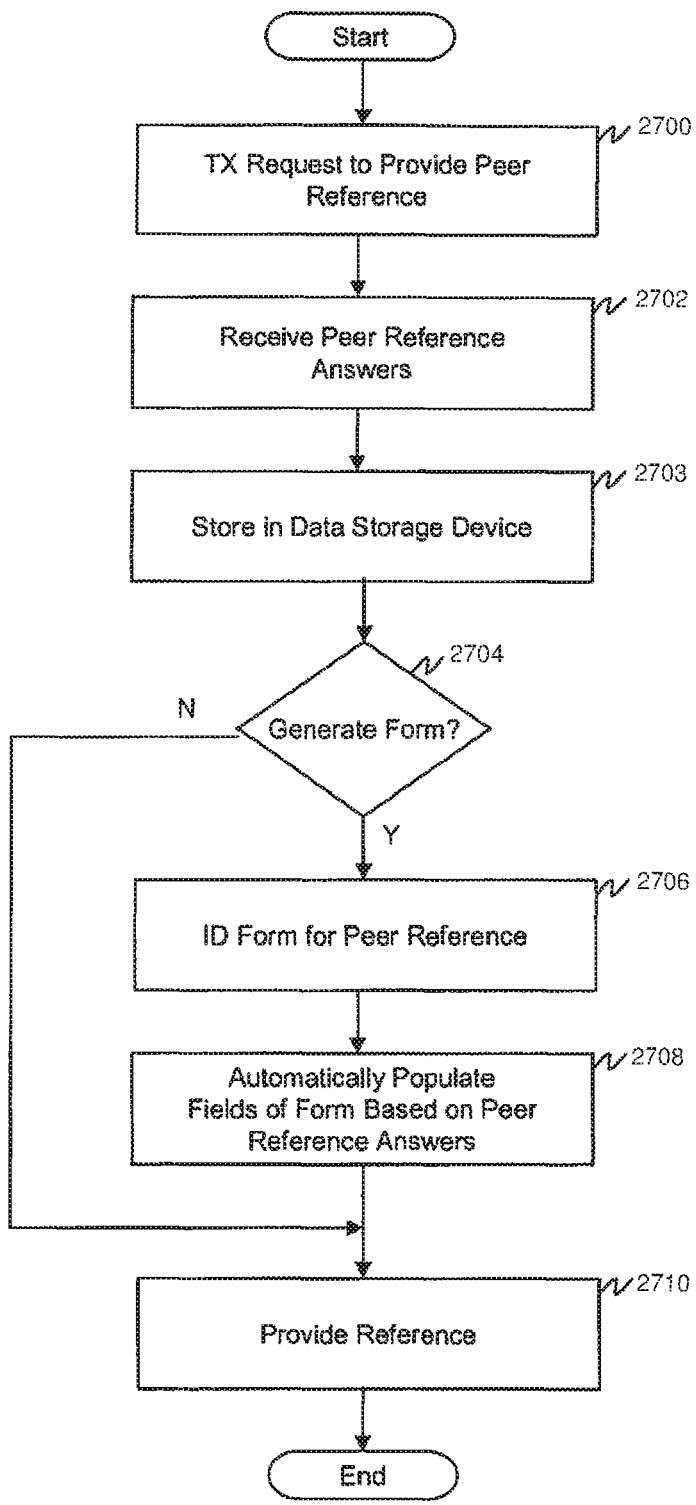
FIG. 30 is a flow diagram of a process for obtaining a peer reference from a qualified peer according to one embodiment of the invention.

FIG. 30 is a flow diagram of a process for obtaining a peer reference from a qualified peer according to one embodiment of the invention. The process may be described in terms of a software routine executed by the processor in the server 100 based on instructions stored in the server's memory. The instructions may also be stored in other non-transient computer readable media such as, for example, a disk, CD, flash drive, or the like. A person of skill in the art should also recognize that the routine may be executed via hardware, firmware (e.g., via an ASIC), or in any combination of software, firmware, and/or hardware. Furthermore, the sequence of steps of the process is not fixed, but can be altered into any desired sequence as recognized by a person of skill in the art.

The process starts, and in step 2700, the online portal 2100b transmits a request to a qualified peer to provide a peer reference for a particular provider. In this regard, the online portal 2100b may display an updated list of qualified peers for the particular provider, and the user may select a peer from the list to whom he or she wishes to send a request for peer referral. According to one embodiment of the invention, the request may be an email message including a link to a peer referral input form which the selected peer is requested to fill out. Alternatively, the request or the form itself may be sent to the peer via email, fax, mail, or any other data communications medium conventional in the art.

In step 2702, the online portal receives the peer reference answers from the peer. Upon receipt, the online portal may optionally be configured to submit the answers to the information sources 2106 to verify that the information is accurate, as is discussed in further detail in the above-referenced U.S. Pat. No. 7,529,682. Such information sources 2106 may be social networking sites, information databases, or any other body of information conventional in the art. Any mechanism for identifying, accessing, and comparing the information may be utilized as will be apparent to a person of skill in the art. The server 2100 may be configured to transmit an alarm to the peer reference or any other entity identified by the server, upon an indication of discrepancy in the information being compared.

In step 2703, the peer reference answers provided in the structured, universal online form is stored in the data storage device 2108. According to one embodiment, the storing in the data storage device 2108 populates objects of a common object model for retrieval when populating specific healthcare referral forms provided by different healthcare entities.

In step 2704 a determination is made as to whether a specific referral form is to be generated based on the provided peer referral. If a form is to be automatically generated, the online portal invokes the forms engine 2100c to identify the appropriate form to generate in step 2706. The identification may be based on manual selection of the form by the user. The form may also be automatically identified by the forms engine 2100c based on an indication by the user as to the ultimate recipient of the peer referral.

After the form to be generated has been identified, the forms engine 2100c, in step 2708, proceeds to pre-populate the selected form based on the peer reference answers from the peer.

In step 2710, the online portal 2100b provides the peer reference information (which could be either the pre-populated form or simply the peer reference answers as submitted by the peer in the universal format), to a recipient indicated by the user. Such recipient may be the user himself, in which case the form is downloaded to the provider device 2102 over the data communications network 2110, and stored locally at the provider device for emailing, printing, or displaying at the provider device. The form may also be transmitted to a healthcare entity 2104 indicated by the user or to some other requesting party, over the data communications network 2110.

The above-referenced U.S. Pat. No. 8,850,304 provides a detailed description of step 2708 for automatically populating a form based on answers provided in a universal format which have been mapped to a common object model. In order to effectuate such mapping, the forms engine 2100c includes a visual mapping tool that displays objects of the common object model as well as fields of the form to be mapped. A user drags and drops one or more of the displayed objects into a mapping area, and drags and drops a field to which the one or more objects are to be mapped. The user also identifies a type of association between the selected objects and the field. A mapping entry is then generated in a map file to map the selected objects to the field. Each completed mapping process produces a structured map file in XML or other standard format with detailed metadata that stores a reference to the specific form that was mapped. The map file and related metadata is then stored in the data storage device 2108.

Figure 31:
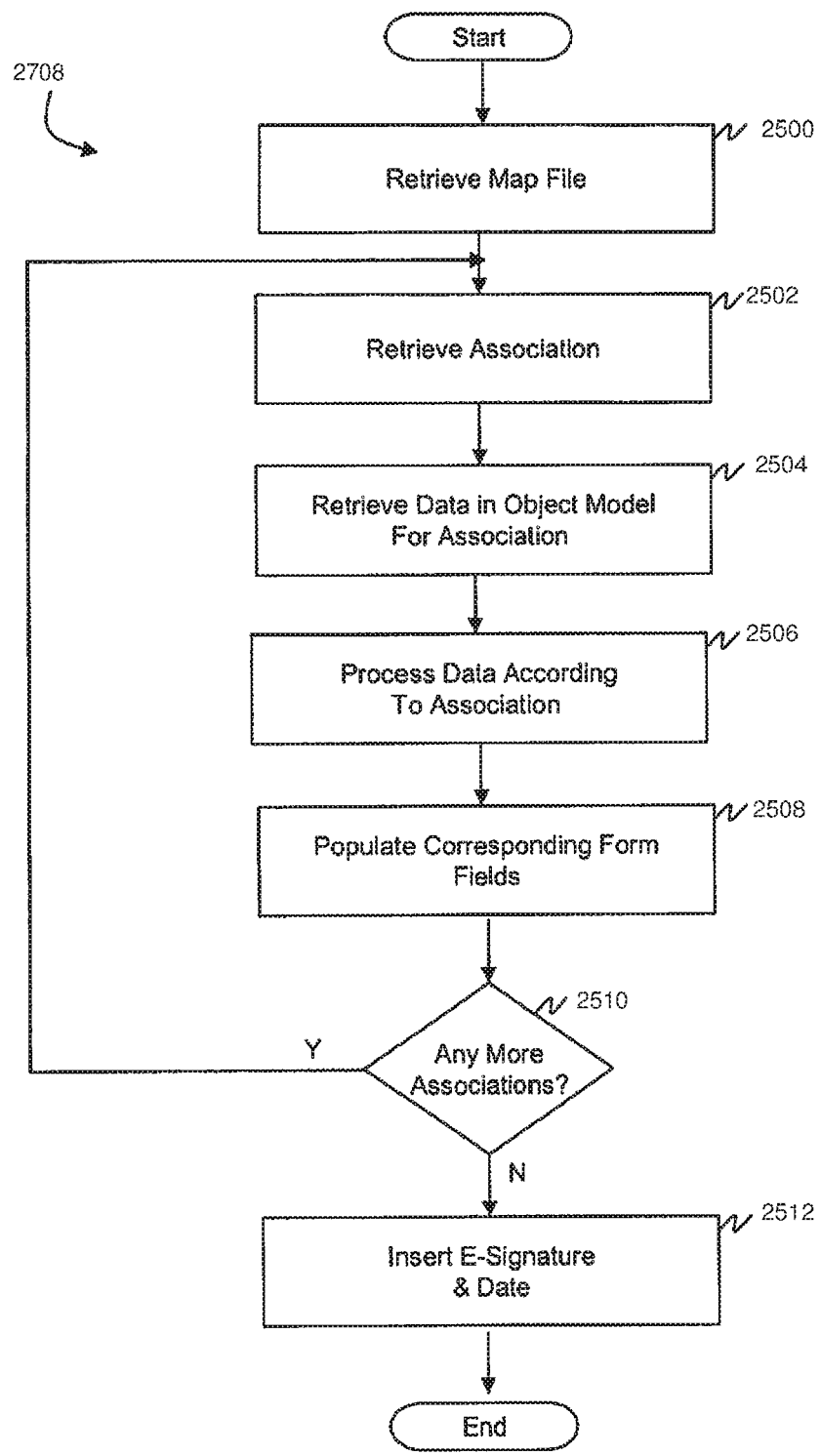
FIG. 31 is a more detailed process flow diagram of a step for generating a form with automatically populated peer reference data according to one embodiment of the invention.

FIG. 31 is a more detailed process flow diagram of step 2708 of generating a form with automatically populated peer reference data according to one embodiment of the invention.

In step 2500, the forms engine 2100c uses the form ID corresponding to the selected referral form, and retrieves a corresponding map file from the mass storage device 2108.

In step 2502, the forms engine 2100c retrieves a stored association from the map file. In this regard, the association identifies the one or more object attributes or properties mapped to a particular field of the form, along with any transformation or aggregation functions that are to be performed for the association.

In step 2504, the forms engine 2100c uses an instantiation of a data access layer and uses the layer components to retrieve data stored for the identified object attribute or property.

In step 2506, the forms engine 2100c processes the retrieved data according to the retrieved association. In this regard, the forms engine 2100c identifies any conversion and/or aggregation rule indicated for the association, and invokes the appropriate algorithm(s) for processing the retrieved data according to the conversion and/or aggregation rule. The processing may be as simple as making a copy of the retrieved data for entering the data as-is into the corresponding form, such as, for example, if the aggregation is a direct mapping of the data. For other types of conversions and/or aggregations, the algorithm may require transformation, derivation, and/or concatenating of the data, as well as inserting spaces or text (e.g., hyphens, commas, semi-colons, etc.).

In step 2508, the forms engine 2100c uses the processed data to automatically populate the corresponding form field.

In step 2510, a determination is made as to whether there are any other associations in the map file that need to be processed for auto-populating the form. If the answer is YES, the forms engine 2100c returns to step 2502 to process the other associations. Otherwise, if the answer is NO, the forms engine 2100c pulls, in step 2512, a stored e-signature of the party providing the peer referral, as well as a date, and enters this information into corresponding fields of the form. The form is then ready to be displayed on the provider device 2102 for review by the provider. The provider may review and make any needed updates to the pre-populated information, and/or manually enter information for any fields that have not been automatically pre-populated. The form is then ready to be downloaded to the provider, or to be submitted directly to a healthcare entity coupled to the server. In this regard, the web portal 2100b may provide a "download" option which causes transmitting a copy of the filled form for storing in a data store coupled to the provider device. The web portal 2100b may also provide a "submit" option which prompts the user to enter information of the entity (e.g., an email address) who is to receive a copy of the filled form.

FIG. 32 is an exemplary screen shot of a screen displaying a universal peer reference form according to one embodiment of the invention. According to one embodiment, the universal peer reference form may be accessed upon receipt of the request message from the requesting user. The particular form to be completed may be identified by a URL link included in the request. Selection of the link by the peer causes a display of the peer reference form as shown in FIG. 32. Alternatively, the peer may, with or without prompting, access the online portal 2100b and navigate to the peer reference page shown in FIG. 32.

According to one embodiment of the invention, instead of a peer completing a specific referral form which may vary from institution to institution, the peer completes the universal reference form, and the forms engine 2100c auto-completes the specific referral forms that may have to be submitted to one or more institutions. In this manner, the peer need not repeat data entry if multiple references need to be submitted to multiple institutions. In this regard, various fields 2300-2306 of the universal form are each mapped to an object of the common object model associated with the form. The objects of the common object model are in turn mapped to fields of specific referral forms maintained in the data storage device 2108. The mapping data is then used to auto-complete the specific referral forms for submitting to the appropriate recipients.

Figure 33:
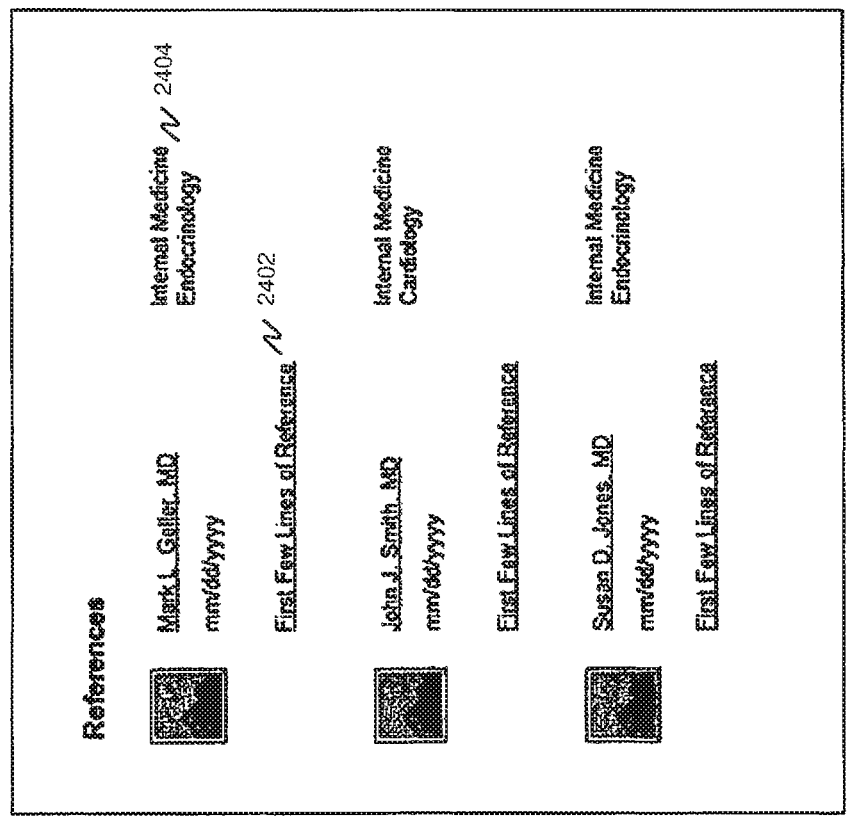
FIG. 33 is an exemplary screen shot of a references page listing various peers for whom peer references have been received according to one embodiment of the invention.

FIG. 33 is an exemplary screen shot of a references page listing various peers for whom peer references have been received according to one embodiment of the invention. A user who has requested and received peer references may access the references page via the online portal 2100b. The user may view all or a portion of information contained in the peer reference by selecting link 2402. Basic information 2404 about the peer providing the reference may also be retrieved from the peer's profile and displayed on the screen.

Although this invention has been described in certain specific embodiments, those skilled in the art will have no difficulty devising variations to the described embodiment which in no way depart from the scope and spirit of the present invention. Furthermore, to those skilled in the various arts, the invention itself herein will suggest solutions to other tasks and adaptations for other applications. For example, although peer referencing is described in the context of healthcare peer referencing, a person of skill in the art should recognize that embodiments of the present invention applies to other disciplines that may require references to be submitted, such as, for example, for job applications, college admissions, and the like. It is the Applicant's intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

Embodiments of the invention in which an exclusive property or privilege is claimed are defined as follows.

The invention claimed is:

1. A method for electronically validating information pertaining to applicants over a communication network including a plurality of computing devices, the method comprising:

collecting credentials information pertaining to applicants in one or more of a plurality of formats;

converting the credentials information in one or more of the plurality of formats into a common format of collected credentials information, the common format having one or more fields, wherein the converting utilizes a common object model and further comprises:

populating said common object model based on the collected credentials information;

identifying a type of association between objects in a mapping area and the fields, wherein the identified type of association is selected from a group consisting of (1) a one-to-one connection between an object and a field when a one-to-one connection exists, and (2) a conversion, including one or more of (a) a derived association, (b) a transformative association and (c) an aggregation based upon attributes from the common object model in a hierarchical object tree, when a one-to-one connection between object and field does not exist;
storing a map file containing said identified type of association;
retrieving the map file, wherein the map file maps fields to objects of the common object model using said identified type of association;
retrieving data mapped to the fields;
processing the retrieved data file for the applicant; and
automatically populating the one or more fields based on the processed data;
storing the collected credentials information in a database;
validating for a plurality of applicants the collected credentials information with external sources through an electronic interface, wherein the validating further comprises:
automatically obtaining third-party credentials data; and
automatically electronically comparing the obtained third party credentials data to the collected credentials information pertaining to an applicant;
automatically electronically updating the database with the retrieved data;
automatically electronically notifying a user of inconsistencies between the obtained third party credentials data and the collected credentials information pertaining to the applicant; and
providing selective electronic access to the third-party credentials data over the communication network to one or more users and to the applicant to which the third-party credentialing data pertains.

2. The method of claim 1 further comprising creating and maintaining a re-validation calendar of said credentials information.

3. The method of claim 1 further comprising identifying adverse information or errors in validation of credentials information.

4. The method of claim 1 further comprising auditing credentials information.

5. The method of claim 1 further comprising generating user-defined reports on credentials information.

6. The method of claim 1 further comprising generating accounting records associated with the validation of credentials information.

7. The method of claim 1 wherein collecting credentials information in a plurality of formats comprises:
creating an applicant record for data storage;
contacting the applicant via email, fax, letter or a combination thereof; and
providing the applicant with reminder renewals for expiring credentials information.

8. The method of claim 1 wherein collecting credentials information comprises collecting responses over the Internet.

9. The method of claim 1 wherein collecting credentials information comprises collecting response information stored on a storage media.

10. The method of claim 1 wherein collecting credentials information comprises importing teleform data.

11. The method of claim 1 wherein collecting credentials information comprises continually requesting credentials information from the applicant via email, fax, letter or a combination thereof until all of the requested credentials information is collected.

12. The method of claim 1 further comprising authenticating the credentials information with an electronic or scanned signature.

13. The method of claim 12 wherein authenticating the credentials information with an electronic signature or scanned signature comprises:
assigning a Global Unique Identification (GUID) upon login; and
capturing the scanned signature from a paper document.

14. The method of claim 1 wherein storing collected credentials information in a dynamic database comprises:
time-stamping collected credentials information;
comparing existing credentials information to newly entered credentials information; and
archiving existing credentials information to a history table.

15. The method of claim 1 further comprising creating client specific dynamic template in accordance with extensible markup language specification and mapping stored credentials information into dynamic template.

16. The method of claim 1 wherein validating collected credentials information with external sources further comprises:
auto-generating validation requests to non-electronic sources; and
receiving validation information from non-electronic sources and storing as scanned images.

17. The method of claim 16 wherein validating collected credentials information with external sources further comprises:
comparing validation information with credentials information submitted by the applicant;
auto-updating the database with matched information;
manually updating the database through use of electronic work ticklers; and
providing real-time notification of adverse information.

18. The method of claim 3 wherein identifying adverse information or errors in validation of credentials information comprises:
requesting explanations for adverse information or errors from the applicant; and
re-validating the credentials information, if warranted.

19. The method of claim 4 wherein auditing credentials information comprises:
(a) performing two consecutive audits of validated credentials information;
(b) performing a quality audit of selected credentials information if each of the two consecutive audits is passed; and
(c) repeating steps (a) and (b) if either of the two consecutive audits is not passed or if the quality audit is not passed.

20. The method of claim 1 further comprising:
generating a list of a plurality of privileges;
establishing criteria for granting said plurality of privileges;
allowing practitioner to select privileges for which he is qualified;
generating delineation of privileges forms from selected privileges; and
auto-sending such delineation of privileges forms to external sources for validation of competence.

21. The method of claim 1 further comprising:
identifying applicants requiring office site review;
performing data entry of office site review results;
generating corrective action plans if required;
tracking completion of corrective action plans; and
generating reports of office site review activities.

22. The method of claim 1 further comprising:
generating a profile of validated credentials information required by regulatory agencies;
notifying affiliated organizations that the credentials information has been validated or re-validated and is complete; and
providing a hyperlink for download of the profile and all copies of electronic and scanned documents utilized during validation.

23. The method of claim 1 further comprising providing the applicants a means to comment on the inconsistencies between the obtained third party credentials data and the collected credentials information pertaining to the applicant.

24. The method of claim 1 wherein the providing selective electronic access comprises making one or more images of primary source data pertinent to the provided information available through download or hyperlink.

25. The method of claim 1 wherein the presenting comprises means for making one or more images of primary source data pertinent to the provided information available through download for hyperlink.

26. The method of claim 1 wherein the presenting comprises means for presenting one or more images of primary source data pertinent to the provided information.

27. The method of claim 1 wherein the querying automatically on a periodic basis third party databases having third party credentials data relating to the collected credentials information comprises continuously querying the third party databases.

28. The method of claim 1, wherein the type of association includes an aggregation rule for aggregating data from a plurality of objects of the common object model, and wherein the processing aggregates the data according to the aggregation rule.

29. The method of claim 1, wherein the type of association includes a conversion rule for converting an aspect of data stored for one or more objects of the common object model, and wherein the processing converts the aspect of the data according to the conversion rule.

30. The method of claim 29, wherein the processing includes converting a format of the data.

31. The method of claim 1, wherein the converting occurs without manual input of data by a user.

32. The method of claim 1 wherein validating collected credentials information comprises verifying the collected credentials information.

33. The method of claim 1 wherein the database is a relational database.

34. The method of claim 33 wherein the relational database is a dynamic relational database.

35. The method of claim 1 wherein the validating step comprises concurrently validating for a plurality of applicants the collected credentials information with external sources through an electronic interface.

36. The method of claim 1 wherein the step of automatically obtaining third-party credentials data comprises querying automatically on a periodic basis third-party databases having third-party credentials data relating to the collected credentials information.

* * * * *